US012239433B2

(12) United States Patent
Otsuki et al.

(10) Patent No.: US 12,239,433 B2
(45) Date of Patent: Mar. 4, 2025

(54) LEARNING SYSTEM, WALKING TRAINING SYSTEM, METHOD, PROGRAM, AND TRAINED MODEL

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP); Hodaka Kito, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 18/583,104

(22) Filed: Feb. 21, 2024

(65) Prior Publication Data

US 2024/0188848 A1    Jun. 13, 2024

Related U.S. Application Data

(62) Division of application No. 16/885,705, filed on May 28, 2020, now Pat. No. 11,944,427.

(30) Foreign Application Priority Data

Jun. 27, 2019  (JP) ................................. 2019-119669

(51) Int. Cl.
*A61B 5/11* (2006.01)
*A61B 5/00* (2006.01)
(Continued)

(52) U.S. Cl.
CPC ............ *A61B 5/1038* (2013.01); *A61B 5/112* (2013.01); *A61B 5/7267* (2013.01); *A61B 5/742* (2013.01);
(Continued)

(58) Field of Classification Search
CPC ..... A61B 5/1038; A61B 5/112; A61B 5/7267; A61B 5/742; A61B 2505/09;
(Continued)

(56) References Cited

U.S. PATENT DOCUMENTS 11,690,534 B2 * 7/2023 Nakashima .......... A61B 5/1038
                                                             600/595
2015/0342820 A1  12/2015 Shimada et al.
(Continued)

FOREIGN PATENT DOCUMENTS

CN      103440368 A  * 12/2013
CN      105286875 A  *  2/2016
(Continued)

OTHER PUBLICATIONS

Aug. 7, 2023 Office Action issued in U.S. Appl. No. 16/885,705.

*Primary Examiner* — Joseph J Dallo
(74) *Attorney, Agent, or Firm* — Oliff PLC

(57) ABSTRACT

The learning system includes a data generation unit configured to generate learning data based on rehabilitation data and a learning unit configured to perform machine learning using the learning data. A sensor is provided to detect a plurality of motion amounts in a walking motion of a trainee, and it is evaluated that, when one of the motion amounts matches one of abnormal walking criteria, that the walking motion is an abnormal walking pattern that meets the matched abnormal walking criterion. The data generation unit generates each of the pieces of rehabilitation data before and after a change in the results of evaluation of the abnormal walking pattern as learning data. The learning unit sequentially inputs each of the pieces of rehabilitation data as one data set, thereby performing machine learning.

6 Claims, 21 Drawing Sheets

(51) Int. Cl.
*A61B 5/103* (2006.01)
*A61H 1/02* (2006.01)
*B25J 9/00* (2006.01)
*G06F 18/214* (2023.01)
*G06N 20/00* (2019.01)
*G06V 10/774* (2022.01)
*G06V 10/776* (2022.01)
*G06V 40/20* (2022.01)
*G16H 50/20* (2018.01)
*G16H 50/30* (2018.01)

(52) U.S. Cl.
CPC .......... *A61H 1/0262* (2013.01); *B25J 9/0006* (2013.01); *G06F 18/2148* (2023.01); *G06N 20/00* (2019.01); *G06V 10/7747* (2022.01); *G06V 10/776* (2022.01); *G06V 40/25* (2022.01); *G16H 50/20* (2018.01); *G16H 50/30* (2018.01); *A61B 2505/09* (2013.01); *A61H 2201/1652* (2013.01); *A61H 2201/5058* (2013.01); *A61H 2205/10* (2013.01)

(58) Field of Classification Search
CPC ... A61B 5/6811; A61B 5/6887; A61B 5/7275; A61B 5/7405; A61B 2562/0252; A61B 5/6828; A61B 5/6829; A61B 5/4836; A61B 2562/0247; A61H 1/0262; A61H 2201/1652; A61H 2201/5058; A61H 2205/10; A61H 2201/0173; A61H 2201/0192; A61H 2201/1207; A61H 2201/163; A61H 2201/1635; A61H 2201/1642; A61H 2201/501; A61H 2201/5043; A61H 2201/5061; A61H 2201/5069; A61H 2201/5084; A61H 2201/5092; A61H 2230/62; A61H 1/00; A61H 1/0237; A61H 1/024; A61H 3/008; A61H 1/0229; A61H 3/00; A61H 2003/007; A61H 2201/50; B25J 9/0006; G06F 18/2148; G06N 20/00; G06N 3/044; G06N 3/045; G06N 3/084; G06V 10/7747; G06V 10/776; G06V 40/25; G16H 50/20; G16H 50/30; G16H 20/30; G16H 40/63

See application file for complete search history.

(56) References Cited

U.S. PATENT DOCUMENTS

| | | | | |
|---|---|---|---|---|
| 2018/0140842 | A1* | 5/2018 | Ó Laighin | A61B 5/1116 |
| 2018/0338710 | A1* | 11/2018 | Tas | A61B 5/1128 |
| 2019/0150792 | A1 | 5/2019 | Nakashima et al. | |
| 2019/0150793 | A1* | 5/2019 | Barth | G06N 3/08 |
| 2020/0030176 | A1* | 1/2020 | Yu | A61H 1/0262 |
| 2022/0118256 | A1* | 4/2022 | Ó Laighin | A61N 1/36003 |

FOREIGN PATENT DOCUMENTS

| | | | | |
|---|---|---|---|---|
| CN | 106539587 | A | 3/2017 | |
| CN | 109793644 | A | 5/2019 | |
| CN | 110320806 | A * | 10/2019 | ........... G05B 13/042 |
| EP | 3257437 | A1 * | 12/2017 | ............ A61B 5/112 |
| JP | 2015-223294 | A | 12/2015 | |
| WO | WO-2011144883 | A1 * | 11/2011 | ............ A61B 5/112 |
| WO | WO-2016188571 | A1 * | 12/2016 | ....... G06F 16/24578 |
| WO | WO-2016205212 | A1 * | 12/2016 | ........... A61B 5/1118 |

* cited by examiner

| STEP | ABNORMAL WALKING PATTERN 1 | ABNORMAL WALKING PATTERN 2 | ... | ABNORMAL WALKING PATTERN 7 |
|---|---|---|---|---|
| 1 | OK | OK | | OK |
| 2 | OK | OK | | OK |
| 3 | NG | OK | | OK |
| 4 | OK | OK | | OK |
| 5 | OK | OK | | OK |
| 6 | OK | OK | | OK |
| 7 | OK | OK | | OK |
| 8 | OK | NG | | NG |
| 9 | OK | NG | | NG |
| ⋮ | ⋮ | ⋮ | | ⋮ |

Fig. 13

| STEP | SETTING PARAMETER 1 | SETTING PARAMETER 2 | . . . | SETTING PARAMETER N |
|---|---|---|---|---|
| 1 | 1 | 50 | | 5 |
| 2 | 1 | 50 | | 5 |
| 3 | 1.5 | 50 | | 5 |
| 4 | 1 | 50 | | 5 |
| 5 | 1 | 50 | | 5 |
| 6 | 1 | 50 | | 5 |
| 7 | 1 | 50 | | 5 |
| 8 | 1 | 60 | | 4 |
| 9 | 1 | 60 | | 4 |
| ⋮ | ⋮ | ⋮ | | ⋮ |

Fig. 15

| DATA SET No. | SETTING PARAMETER | DETERMINATION DATA | TRAINEE DATA |
|---|---|---|---|
| 1 | parameter_1 | determination_1 | USER_1 |
| 2 | parameter_2 | determination_2 | USER_1 |
| 3 | parameter_3 | determination_3 | USER_1 |
| 4 | parameter_4 | determination_4 | USER_1 |
| ⋮ | ⋮ | ⋮ | ⋮ |

Fig. 16

| DATA SET No. | SETTING PARAMETER | DETECTION DATA |
|---|---|---|
| 1 | parameter_1 | sensor_1 |
| 2 | parameter_2 | sensor_2 |
| 3 | parameter_3 | sensor_3 |
| 4 | parameter_4 | sensor_4 |
| ⋮ | ⋮ | ⋮ |

← SETTING PARAMETER CHANGE (at row 2)

AVERAGE (rows 2–4)

Fig. 21

LEARNING SYSTEM, WALKING TRAINING SYSTEM, METHOD, PROGRAM, AND TRAINED MODEL

CROSS REFERENCE TO RELATED APPLICATIONS

This application is a divisional application of U.S. patent application Ser. No. 16/885,705 filed May 28, 2020, which claims the benefit of priority from Japanese patent application No. 2019-119669, filed on Jun. 27, 2019, the disclosure of which is incorporated herein in its entirety by reference.

BACKGROUND

The present disclosure relates to a learning system, a walking training system, a method, a program, and a trained model.

Japanese Unexamined Patent Application Publication No. 2015-223294 discloses a walking training apparatus.

SUMMARY

In the above walking training apparatus, it is desired that a trainee be able to perform walking training more appropriately.

The present disclosure has been made in order to solve the above-described problem and provides a learning system, a walking training system, a method, a program, and a trained model for allowing a trainee to perform walking training appropriately.

A learning system according to this embodiment includes: a data acquisition unit configured to acquire rehabilitation data from a walking training system including an actuator configured to assist a walking motion of a trainee, a sensor configured to detect data regarding the walking motion assisted by the actuator, and a control unit configured to control the actuator in accordance with a setting parameter; a data generation unit configured to generate learning data based on the rehabilitation data; and a learning unit configured to perform machine learning using the learning data, in which the sensor is provided to detect a plurality of motion amounts in the walking motion of the trainee, it is evaluated that, for each walking cycle of the walking motion, when at least one of the motion amounts matches one of predetermined abnormal walking criteria, the walking motion of the trainee is an abnormal walking pattern that meets the matched abnormal walking criterion, the data generation unit generates each of the pieces of rehabilitation data in a walking cycle before and after a change in results of evaluation of the abnormal walking pattern as learning data, the learning unit sequentially inputs each of the pieces of rehabilitation data in the walking cycle before and after the change in the results of the evaluation as one data set, thereby performing machine learning, and the learning unit constructs a learning model that receives the abnormal walking pattern and outputs the setting parameter.

In the aforementioned learning system, it may be determined whether the walking motion of the trainee matches the abnormal walking criteria using an average value of motion amounts for a plurality of walking cycles shortly after the change in the setting value of the setting parameter.

In the aforementioned learning system, when setting values of two or more of the aforementioned setting parameters change at the same time in consecutive walking cycles, the learning unit may weight each of these two or more of the aforementioned setting parameters changed at the same time.

A learning method according to this embodiment includes the steps of: acquiring rehabilitation data from a walking training system including an actuator configured to assist a walking motion of a trainee, a sensor configured to detect data regarding the walking motion assisted by the actuator, and a control unit configured to control the actuator in accordance with a setting parameter; generating learning data based on the rehabilitation data; and performing machine learning using the learning data, in which the sensor is provided to detect a plurality of motion amounts in the walking motion of the trainee, it is evaluated that, for each walking cycle of the walking motion, when at least one of the motion amounts matches one of predetermined abnormal walking criteria, the walking motion of the trainee is an abnormal walking pattern that meets the matched abnormal walking criterion, each of the pieces of rehabilitation data in a walking cycle before and after a change in results of evaluation of the abnormal walking pattern is generated as learning data, each of the pieces of rehabilitation data in the walking cycle before and after the change in the results of the evaluation is sequentially input as one data set, thereby performing machine learning, and a learning model that receives the abnormal walking pattern and outputs the setting parameter is constructed.

A program according to this embodiment causes a computer to execute the aforementioned learning method.

A trained model according to this embodiment is a trained model for causing a computer to function so as to output a setting parameter that is associated with a matched abnormal walking pattern based on rehabilitation data for evaluation acquired in a walking training system, in which the trained model is a learning model generated in the aforementioned learning system.

A walking training system according to this embodiment includes: an actuator configured to assist a walking motion of a trainee; a sensor provided to detect a plurality of motion amounts in the walking motion of the trainee assisted by the actuator; a control unit configured to control the actuator in accordance with a plurality of setting parameters, an evaluation unit configured to evaluate that, for each of walking cycles of the walking motion, when at least one of the motion amounts matches one of a plurality of predetermined abnormal walking criteria, the walking motion in the walking cycle is an abnormal walking pattern that meets the abnormal walking criterion; and an output unit configured to receive the abnormal walking pattern and outputs the setting parameter associated with the abnormal walking pattern.

In the aforementioned walking training system, it may be determined whether the walking motion of the trainee matches the abnormal walking criteria using an average value of motion amounts for a plurality of walking cycles shortly after the change in the setting value of the setting parameter.

In the aforementioned walking training system, the output unit may output the setting parameter using the aforementioned trained model.

An operation method of a walking training system according to this embodiment is an operation method of a walking training system including: an actuator configured to assist a walking motion of a trainee; a sensor provided to detect a plurality of motion amounts in the walking motion of the trainee assisted by the actuator; a control unit configured to control the actuator in accordance with a plurality of setting parameters, the operation method including the steps of:

evaluating, for each of walking cycles of the walking motion, when at least one of the motion amounts matches one of a plurality of predetermined abnormal walking criteria, that the walking motion in the walking cycle is an abnormal walking pattern that meets the abnormal walking criterion; and receiving the abnormal walking pattern and outputting the setting parameter associated with the abnormal walking pattern.

In the aforementioned operation method of the walking training system, it may be determined whether the walking motion of the trainee matches the abnormal walking criteria using an average value of motion amounts for a plurality of walking cycles shortly after the change in the setting value of the setting parameter.

In the aforementioned operation method of the walking training system, the setting parameter may be output using the aforementioned trained model.

According to the present disclosure, it is possible to provide a learning system, a walking training system, a method, a program, and a trained model for allowing a trainee to perform walking training appropriately.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 13 is a table illustrating results of determination of abnormal walking;

FIG. 15 is a table illustrating a change in setting parameters;

FIG. 16 is a table illustrating learning data sets;

FIG. 21 is a table illustrating processing of the modified example.

DESCRIPTION OF EMBODIMENTS

Hereinafter, the present disclosure will be explained through embodiments of the present disclosure. However, they are not intended to limit the scope of the present disclosure according to the claims. Further, not all of the components/structures described in the embodiments are necessarily indispensable as means for solving the problem.

First Embodiment

Hereinafter, with reference to the drawings, a first embodiment will be described.
(System Configuration)

Figure 1:
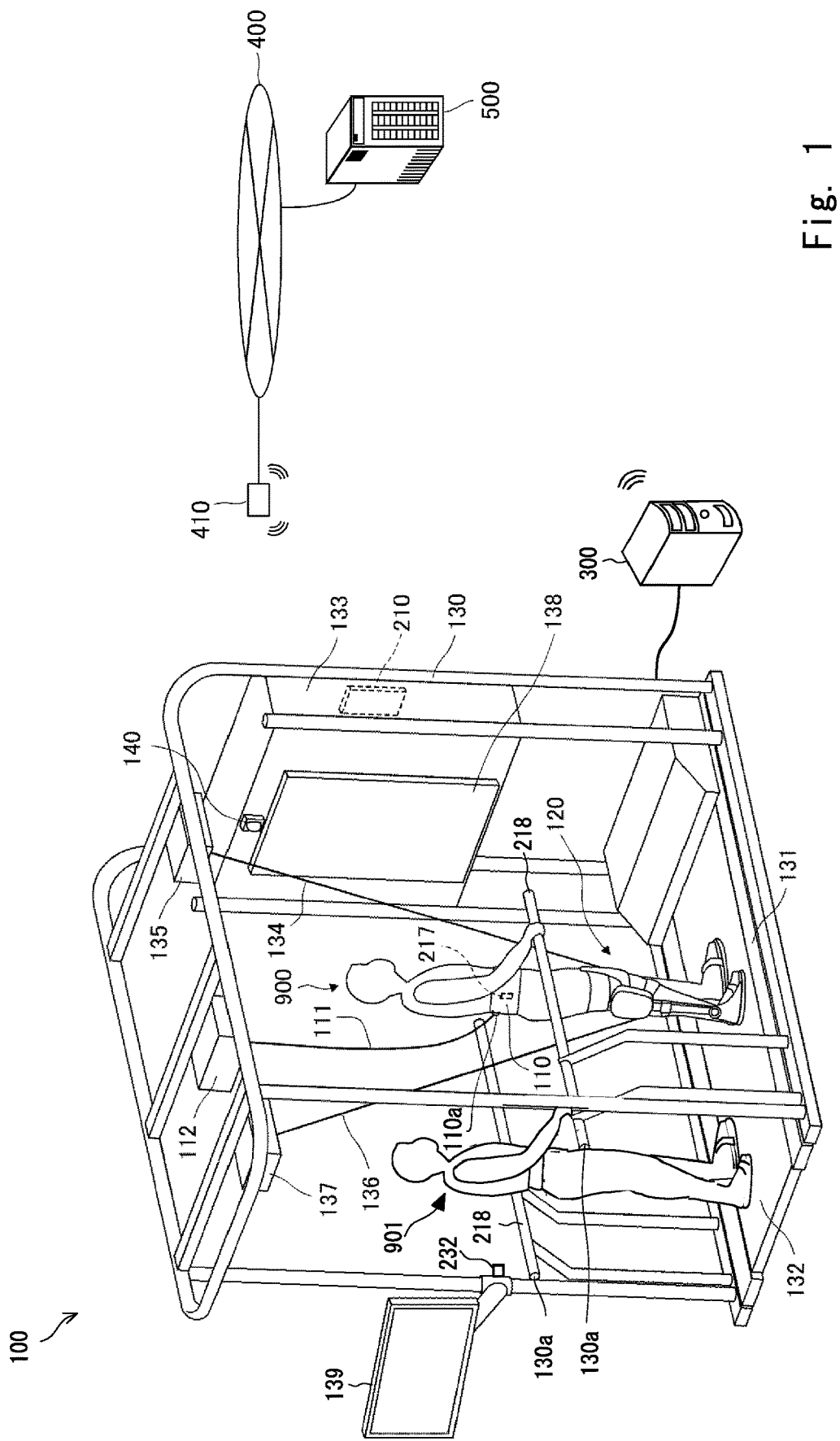
FIG. 1 is a schematic perspective view of a walking training apparatus according to an embodiment.

FIG. 1 is a general concept diagram showing an example of a configuration of a rehabilitation support system according to a first embodiment. The rehabilitation support system (a walking training system) according to this embodiment mainly includes a walking training apparatus (system) 100, an external communication apparatus 300, and a server (a server apparatus) 500. Note that the server 500 may be an external server that can communicate with the walking training apparatus 100 or may be embedded in the walking training apparatus 100 itself. That is, the walking training apparatus 100 may or may not include the server 500. A trained model that will be described later may be incorporated in the external server 500 or may be incorporated in the walking training apparatus 100.

The walking training apparatus 100 is a specific example of a rehabilitation support apparatus that supports rehabilitation performed by a trainee (a user) 900. The walking training apparatus 100 is an apparatus by which the trainee 900, who is, for example, a hemiplegic patient suffering from paralysis in one of his/her legs, performs walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like.

The walking training apparatus 100 mainly includes a control panel 133 attached to a frame 130 forming an overall framework, a treadmill 131 on which the trainee 900 walks, and a walking assistance apparatus 120 attached to a diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who performs the walking training, gets on the belt 132 and tries walking in accordance with the movement of the belt 132. Note that the training staff member 901 can stand on the belt 132 behind the trainee 900 and walk together with the trainee 900 as shown in FIG. 1. However, the training staff member 901 may typically be in a state in which he/she can easily assist the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows the degree of progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the right and left sides of the trainee 900. Each of the handrails 130a is orientated in a direction parallel to the walking direction of the trainee 900. The vertical position and the right/left position of the handrails 130a are adjustable. That is, the handrails 130a may include a mechanism for changing its height and width. Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

A camera 140 functions as an image pickup unit for observing the whole body of the trainee 900. The camera 140 is disposed near the training monitor 138 and positioned so as to face the trainee. The camera 140 takes still images and moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). According to the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of the trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed on its surface. The management monitor 139 displays various menu items related to the training settings, various parameter values during the training, training results, and so on. Further, an emergency stop button 232 is provided near the management monitor 139. When the training staff member 901 pushes the emergency stop button 232, the walking training apparatus 100 immediately stops its operation.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load on the sole of the foot, and outputs various kinds of data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

The overall control unit 210 generates rehabilitation data that may include setting parameters related to the training settings, various kinds of data related to the moving leg output from the walking assistance apparatus 120 as a result of training, and so on. The rehabilitation data may include, for example, data indicating the training staff member 901 or indicating his/her years of experience, level of proficiency, etc., data indicating the symptom, the walking ability, the degree of recovery, etc., of the trainee 900, various kinds of data output from sensors and the like provided outside the walking assistance apparatus 120. Note that details of the rehabilitation data will be described later.

The external communication apparatus 300 is a specific example of transmission means for transmitting the rehabilitation data to the outside. The external communication apparatus 300 may have a function of receiving and temporarily storing rehabilitation data output from the walking training apparatus 100 and a function of transmitting the stored rehabilitation data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network). Note that the walking training apparatus 100 may be equipped with a communication apparatus instead of using the external communication apparatus 300.

The server 500 is a specific example of storage means for storing the rehabilitation data. The server 500 is connected to the network 400 and has a function of accumulating the rehabilitation data received from the external communication apparatus 300. The function of the server 500 will be described later.

In the first embodiment, the walking training apparatus 100 is described as an example of the rehabilitation support apparatus. However, the rehabilitation support apparatus is not limited to the one described in this example and may be an arbitrary rehabilitation support apparatus that supports rehabilitation performed by a trainee. For example, the rehabilitation support apparatus may be an upper-limb rehabilitation support apparatus that supports rehabilitation of a shoulder(s) or an arm(s). Alternatively, the rehabilitation support apparatus may be a rehabilitation support apparatus that supports rehabilitation for a balancing ability of a trainee.

Figure 2:
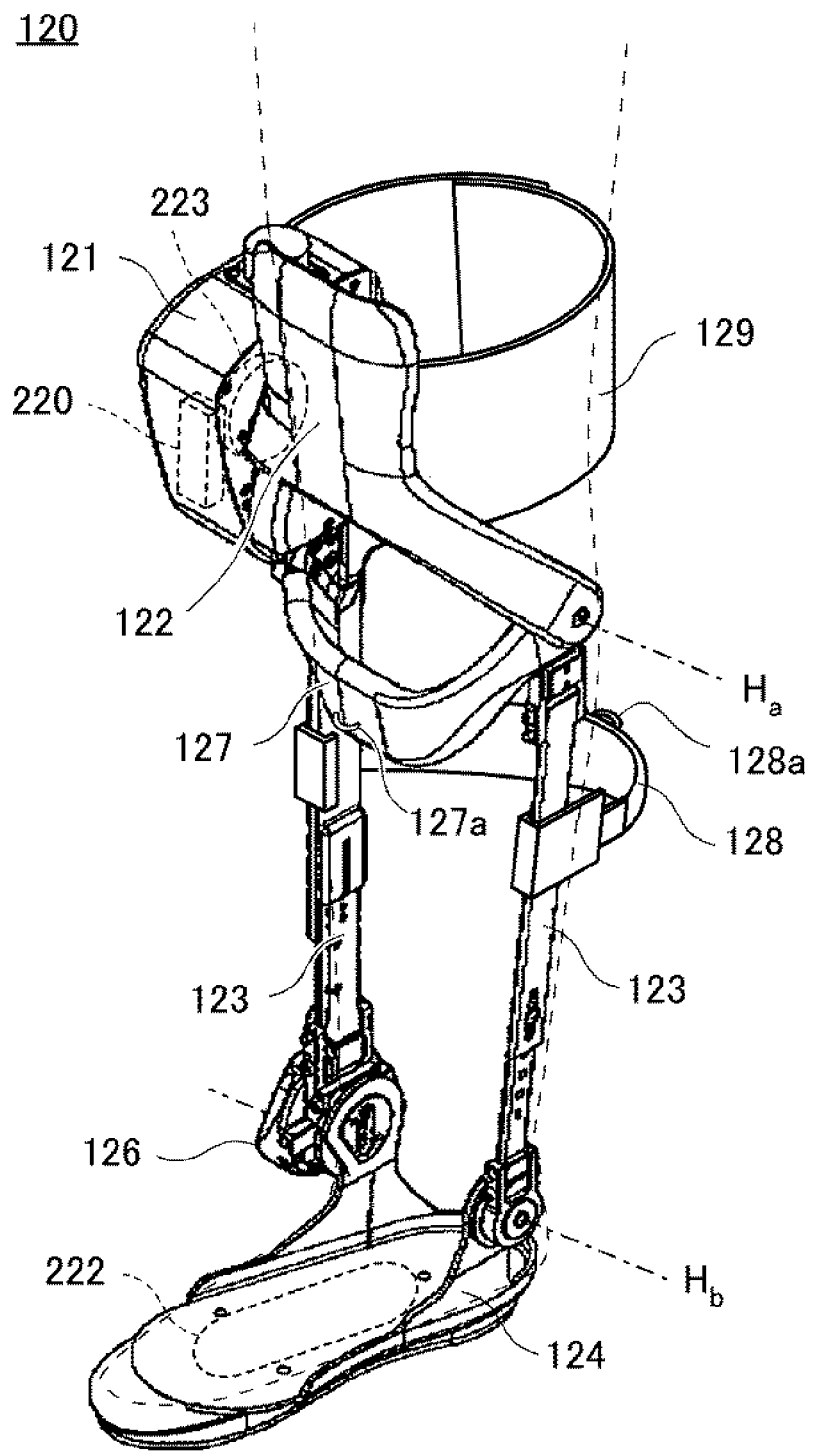
FIG. 2 is a schematic perspective view of a walking assistance apparatus.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of the diseased leg, and a load sensor 222 for detecting a load applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, include an upper-leg frame 122 and a lower-leg frame 123 rotatably connected to the upper-leg frame 122. Further, the frames also include a sole frame 124 rotatably connected to the lower-leg frame 123, a front connection frame 127 for connecting the front wire 134, and a rear connection frame 128 for connecting the rear wire 136.

The upper-leg frame 122 and the lower-leg frame 123 rotate relative to each other around a hinge axis $H_a$ shown in FIG. 2. The motor of the control unit 121 rotates according to an instruction from the assistance control unit 220, and by doing so, force the upper-leg frame 122 and the lower-leg frame 123 to open relative to each other around the hinge axis $H_a$ or force them to close relative to each other. An angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the right/left direction in front of the upper leg and is connected to the upper-leg frame 122 at both ends. Further, a connection hook 127a for connecting the front wire 134 is provided at or near the center of the front connection frame 127 in the right/left direction. The rear connection frame 128 is disposed so as to extend in the right/left direction behind the lower leg and is connected to the lower-leg frame 123 at both ends. The lower-leg frame 123 can extend in a vertical direction. Further, a connection hook 128a for connecting the rear wire 136 is provided at or near the center of the rear connection frame 128 in the right/left direction.

The upper-leg frame 122 includes an upper-leg belt 129. The upper-leg belt 129 is a belt integrally provided in the upper-leg frame 122 and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
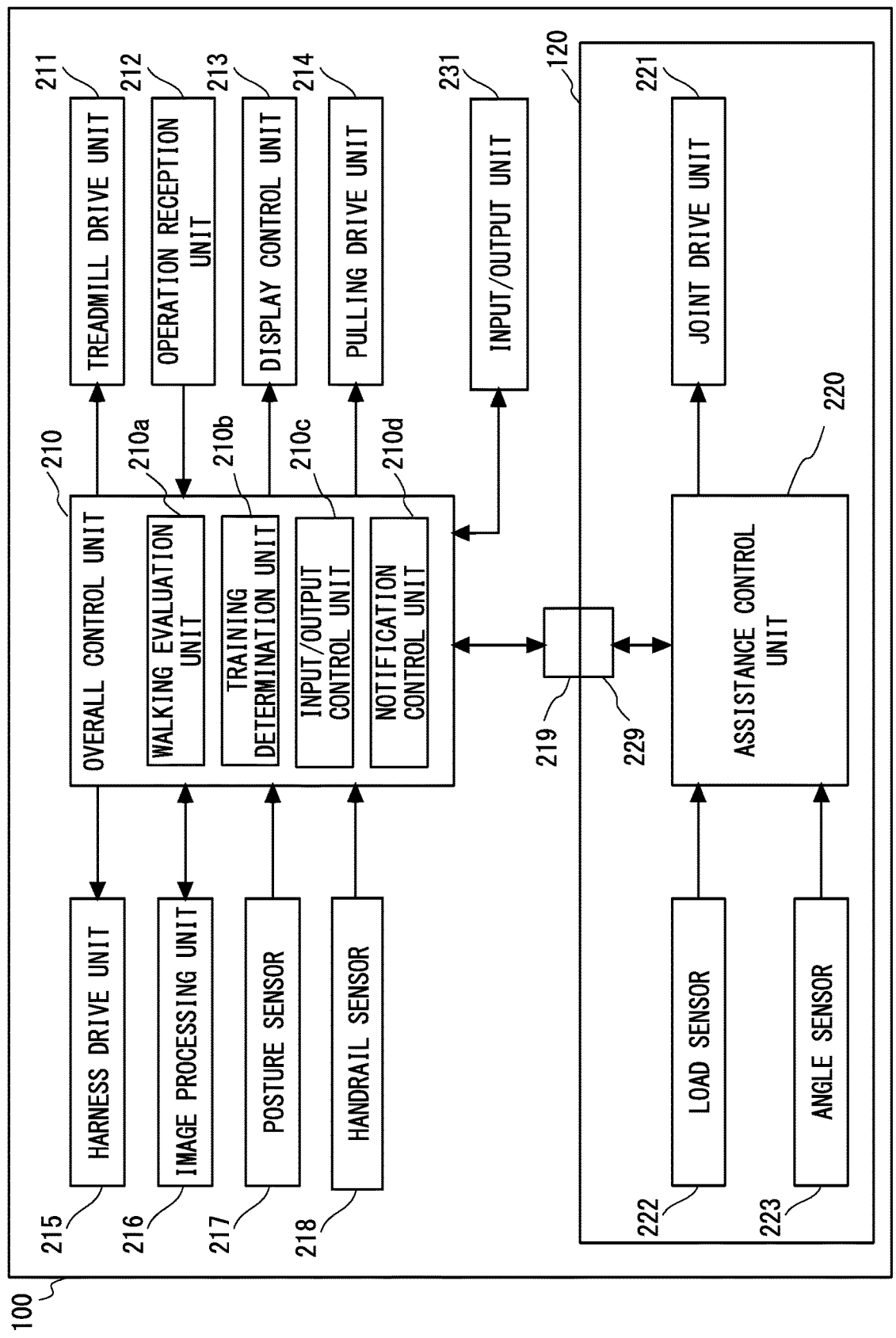
FIG. 3 is a diagram showing a system configuration of the walking training apparatus.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed on the management monitor 139, an accessory remote controller, etc., which constitute the operation reception unit 212. According to the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing the degree of progress of the training and a real-time video image shot by the camera 140 in accordance with the display signal.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies, for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The overall control unit 210 also serves as a function execution unit that performs various arithmetic operations and controls related to the overall control. The walking evaluation unit 210a evaluates whether the walking motion of the trainee 900 is abnormal or not by using data acquired from various sensors. The training determination unit 210b determines a training result of a series of walking trainings based on, for example, a cumulative number of the abnormal walking evaluated by the walking evaluation unit 210a. The overall control unit 210 can generate, as part of the rehabilitation data, a result of this determination or the cumulative number of the abnormal walking, based on which the results of the determination have been obtained.

Note that the determination method, including its criterion, is not limited to any particular methods. For example, the determination can be made by comparing an amount of movement of the paralyzed body part with a reference value in each walking phase. Note that the walking phases are defined, for example, by classifying one walking cycle of the diseased leg (or a normal leg) into a stance phase in a stance state, a transition phase from the stance phase to a swing phase in a swing state, the swing phase, a transition phase from the swing phase to the stance phase, etc. The walking phase can be classified (determined) based on, for example, the detection result of the load sensor 222 as described above. Note that although the walking cycle can be regarded as one cycle including a stance phase, a transitional phase, a swing phase, and another transitional phase as described above, any one of these phases can be defined as the start phase.

Alternatively, the walking cycle can be regarded as one cycle including, for example, a double-leg support state, a single-leg (diseased-leg) support state, a double-leg support state, and a single-leg (normal-leg) support state. Even in this case, any state may be defined as the start state.

Further, the walking cycle in which attention is paid to the right leg or the left leg (the normal leg or the diseased leg) can be further subdivided. For example, the stance phase can be divided into an initial ground contact and other four sub-phases, and the swing phase can be divided into three sub-phases. The initial ground contact means a moment when the observed foot touches the floor, and the four sub-phases of the stance phase means a load response phase, a mid-stance phase, a terminal stance phase, and a pre-swing phase. The load response phase is a period from the initial ground contact to when the opposite foot comes off the floor (opposite-foot-off). The mid-stance phase is a period from the opposite-foot-off to when the heel of the observed foot comes off the floor (heel-off). The terminal stance phase is a period from the heel-off to an initial ground contact on the opposite side. The pre-swing phase is a period from the initial ground contact on the opposite side to when the observed foot comes off the floor (foot-off). The three sub-phases of the swing phase mean an initial swing phase, a mid-swing phase, and a terminal swing phase. The initial swing phase is a period from the end of the pre-swing phase (the aforementioned foot-off) to when both feet cross each other (foot crossing). The mid-swing phase is a period from the foot crossing to when the tibia becomes vertical (vertical tibia). The terminal swing phase is a period from the vertical tibia to the next initial ground contact.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program supplied from the overall control unit 210. Further, the assistance control unit 220 notifies the overall control unit 210 of the state of the walking assistance apparatus 120 through the communication connection IFs 229 and 219. Further, the assistance control unit 220 performs control of the walking assistance apparatus 120, such as the start/stop thereof, in response to a command from the overall control unit 210.

The joint drive unit 221 includes a motor of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The load sensor 222 detects the magnitude and the distribution of the vertical load applied to the sole of the trainee 900 and transmits a detection signal to the assistance control unit 220 as described above. The assistance control unit 220 receives and analyzes the detection signal, and thereby determines the swing/stance state and estimates the switching therebetween.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (the external communication apparatus 300 or another external apparatus). The input/output control unit 210c of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output controller 210c. For example, the input/output control unit 210c can control the transmission of rehabilitation data to the server 500 and the reception of a command from the server 500 through the input/output unit 231 and the external communication apparatus 300.

When it is necessary to provide a notification to the training staff member 901, the notification control unit 210d provides the notification from the management monitor 139 or a separately-provided speaker(s) by controlling the display control unit 213 or a separately-provided sound control unit or the like. The aforementioned situation where it is necessary to provide a notification to the training staff member 901 may be a situation where a command for providing a notification is received from the server 500. Details of this notification will be described later.

Next, the server 500 will be described in detail.

As described above, the walking training apparatus 100 transmits various kinds of rehabilitation data to the server 500 through the external communication apparatus 300. The server 500 may be configured so as to receive rehabilitation data from a plurality of walking training apparatuses 100. In this way, the server 500 can collect a number of pieces of rehabilitation data. Further, the server 500 is a processing apparatus that processes various kinds of data. For example, the server 500 can function as a learning apparatus (a learning machine or a learning system) that constructs a trained model by performing machine learning by using collected rehabilitation data. Note that the learning apparatus may also be referred to as a learning model generation apparatus.

Figure 4:
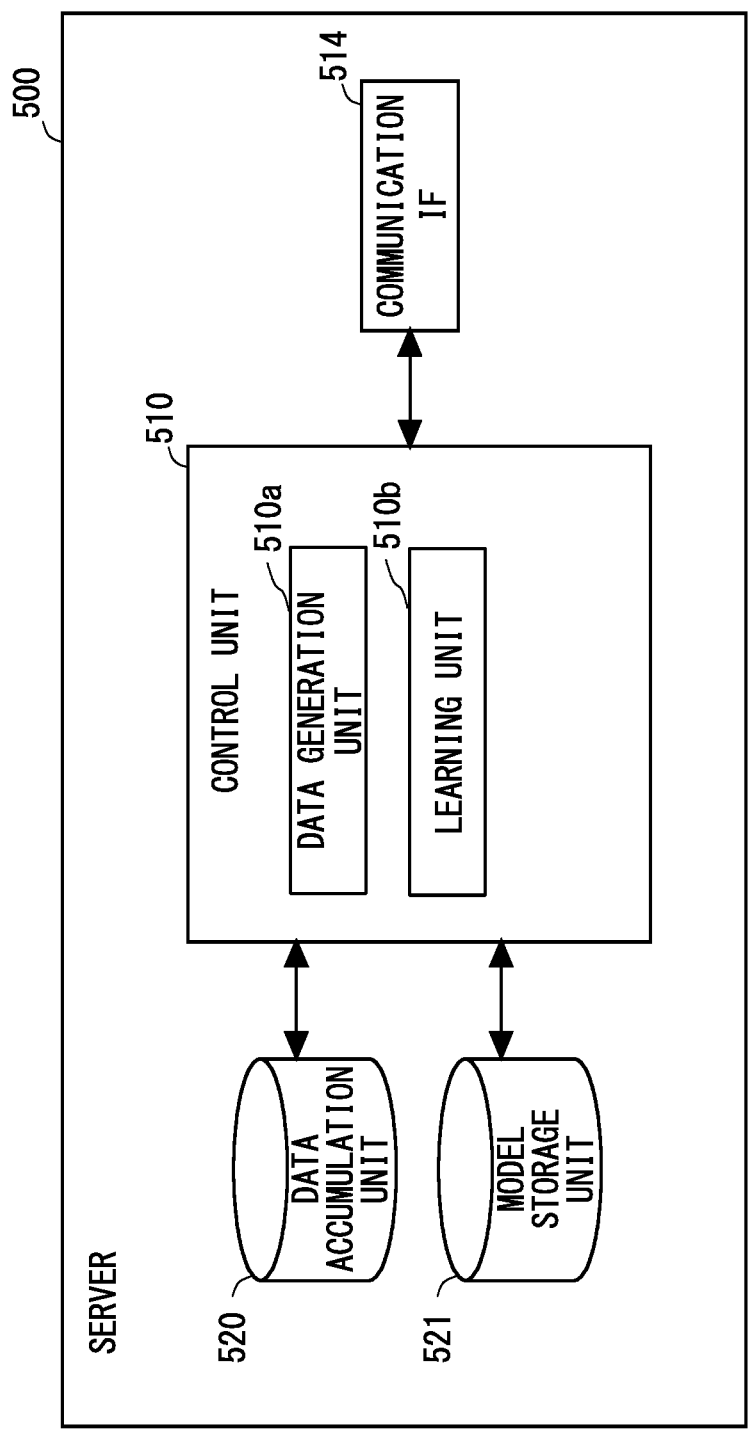
FIG. 4 is a block diagram showing a configuration of a server.

FIG. 4 is a block diagram showing an example of a configuration of the server 500. As shown in FIG. 4, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 includes a data generation unit 510a and a learning unit 510b. In this case, the above-described control program includes a program(s) for implementing the functions of the aforementioned data generation unit 510a and the learning unit 510b.

The communication IF 514 includes, for example, a wired LAN interface and is a communication interface for connecting to the network 400. The control unit 510 can receive rehabilitation data from the walking training apparatus 100 and transmit a command to the walking training apparatus 100 through the communication IF 514.

The data accumulation unit 520 includes a storage device such as an HDD (hard disk drive) or an SSD (solid state drive) and stores rehabilitation data therein. The control unit 510 writes the rehabilitation data received from the external communication apparatus 300 into the data accumulation unit 520 through the communication IF 514. The communication IF 514 and the data accumulation unit 520 each serve, for example, as a data acquisition unit that acquires the rehabilitation data.

Similarly, the model storage unit 521 includes a storage device such as an HDD or an SSD. Note that the data accumulation unit 520 and the model storage unit 521 may include a common storage device. The model storage unit 521 stores at least one of a learning model that has not yet been trained (including those under training) (hereinafter referred to as an untrained model) and a learning model that has already been trained (hereinafter referred to as a trained model). When the server 500 functions as a learning apparatus, at least an untrained model is stored in the model storage unit 521. When the server 500 performs a rehabilitation support process in cooperation with the walking training apparatus 100, at least an operable trained model is stored in the model storage unit 521.

Further, the control unit 510 may be configured so as to perform control to switch between a function as a learning apparatus and a function for performing a rehabilitation support process by using a trained model. Note that the servers 500 may be distributed to (or divided into) an apparatus that is used in a learning stage and an apparatus that is used in an operation stage in which a trained model is used. The data generation unit 510a and the learning unit 510b are provided in order to enable the server 500 to function as a learning apparatus.

(Rehabilitation Data)

Prior to describing the data generation unit 510a and the learning unit 510b, rehabilitation data that the server 500 can collect for learning or for the rehabilitation support process is described hereinafter. The rehabilitation data that the server 500 can collect mainly includes (1) setting parameters of the walking training apparatus 100, (2) detection data detected by sensors and the like provided in the walking training apparatus 100, (3) data related to the trainee 900, and (4) data related to the training staff member 901. The rehabilitation data of the above-described items (1) to (4) may be collected in association with their acquisition date and time. Further, the detection data or the setting parameter may be collected as time-series log data. Alternatively, the detection data or the setting parameter may be, for example, feature values extracted from data acquired at certain time intervals.

The rehabilitation data is mainly data that is obtained by an operation input, an automatic input, measurement by a sensor or the like in the walking training apparatus 100. Further, the rehabilitation data may also include recorded image data recorded by the camera 140. Note that the rehabilitation data may be data acquired on each day of rehabilitation. In this case, the rehabilitation data can be referred to as daily report data. In the following description, it is assumed that the server 500 collects rehabilitation data generated by the walking training apparatus 100. However, it is also possible to configure the server 500 so as to acquire a part of rehabilitation data from an apparatus other than the walking training apparatus 100 such as another server. Here, the part of the rehabilitation data may be, for example, a detail of data of the above-described item (3) such as a symptom of the trainee 900, or a detail of data of the above-described item (4) such as years of experience of a PT (Physical Therapist). The former one can be stored in other servers as medical record information of the trainee 900 and the latter one can be stored in other servers as a personal history of a PT.

In the learning stage, the server 500 may receive rehabilitation data from the walking training apparatus 100 when rehabilitation data is generated or at regular intervals such as on every day or in every week. The type of rehabilitation data to be used (the content included in rehabilitation data) in the learning stage may be different from that in the operation stage. For example, in the operation stage, the server 500 may receive rehabilitation data from the walking training apparatus 100 at the start of training, and may receive data of the above-described item (1) or (2) that is changed during the training. Further, the transmission and the reception of rehabilitation data may be initiated by either the walking training apparatus 100 or the server 500.

The above-described item (1) is described.

The data of the above-described item (1) can be defined as training data of the trainee 900 that is acquired during rehabilitation in the walking training apparatus 100 together with the detection data of the above-described item (2).

The setting parameters of the walking training apparatus 100 are, for example, data that is input by an operator or automatically set in order to define the actions performed by the walking training apparatus 100. Note that as described above, it is assumed that the operator is typically the training staff member 901 who actually attends the training of the trainee 900. Therefore, the following description is given on the assumption that the operator is the training staff member 901. Further, the training staff member 901 is often a PT (Physical Therapist). Therefore, the training staff member 901 may also be referred to simply as the "PT" in the following description.

The setting parameters relate to setting of the actuator. In the walking training apparatus 100, the level of difficulty of walking training can be adjusted by the setting parameters. The overall control unit 210 controls, for example, the actuator such as a motor in accordance with the setting parameters. Note that the setting parameters may include a parameter indicating the level of difficulty, and in this case, some or all of the other setting parameters may be changed according to the change in the level of difficulty. The training staff member 901 increases the level of difficulty of the walking training as the trainee 900 recovers. That is, the training staff member 901 reduces the assistance provided by the walking training apparatus 100 as the walking ability of the trainee 900 improves. Further, the training staff member 901 increases the assistance when an abnormality is found during the walking training. As the training staff member 901 appropriately adjusts the setting parameters, the trainee 900 can perform appropriate walking training and hence perform the rehabilitation more effectively.

Specific examples of the setting parameters are shown hereinafter.

Examples of the setting parameters include a partial weight-supported amount [%], vertical positions of the handrails 130a [cm], right/left positions of the handrails 130a [cm], presence/absence of a hip joint, foot joint plantar flexion limitation [deg], and foot joint dorsiflexion limitation [deg]. Further, the examples of the setting parameters also include a treadmill speed [km/h], swinging assistance [level], and a swinging forward/backward ratio [forward/backward]. Further, the examples of the setting parameters also include knee extension assistance [level], a knee flexing angle [deg], a knee flexing/extending time [sec], a wedge thickness (or a shoe lift) [mm], a weight-off threshold [%], and a load threshold [%]. Note that any type of unit may be used as the unit of data included in rehabilitation data, including the above-shown setting parameters.

The partial weight-supported amount is a ratio at which the weight of the trainee 900 is supported by making the harness pulling unit 112 pull the harness wire 111. The training staff member 901 sets the partial weight-supported amount to a lower value as the desired level of difficulty of the walking training increases. The vertical positions and the right/left positions of the handrails 130a are amounts of adjustments of the handrails 130a from reference positions. The presence/absence of a hip joint is whether or not the hip joint is attached. The foot joint plantar flexion limitation and the foot joint dorsiflexion limitation define an angular range in which the lower-leg frame 123 and the sole frame 124 can rotate around the hinge axis $H_b$. The foot joint plantar flexion limitation corresponds to an upper-limit angle on the front side and the foot joint dorsiflexion limitation corresponds to a maximum angle on the rear side. That is, the foot joint plantar flexion limitation and the foot joint dorsiflexion limitation are limit values of angles at which the foot joint is bent in a direction in which the toe is lowered and a direction in which the toe is raised, respectively. The training staff member 901 sets the values of the foot joint plantar flexion limitation and the foot joint dorsiflexion limitation so that the angular range increases as the desired level of difficulty of the walking training increases.

The treadmill speed is a walking speed on the treadmill 131. The training staff member 901 sets the treadmill speed to a higher value as the desired level of difficulty of the walking training increases. The swinging assistance is a level corresponding to the pulling force applied by the front wire 134 when the leg is swung. Further, the maximum pulling force is increased as this level is raised. The training staff member 901 sets the swinging assistance to a lower level as the desired level of difficulty of the walking training increases. The swinging forward/backward ratio is a ratio between the pulling force by the front wire 134 and the pulling force by the rear wire 136 when the leg is swung.

The knee extending assistance is a level corresponding to the driving torque of the joint drive unit 221 that is applied to prevent the knee from buckling during the stance state. Further, the driving torque is increased as this level is raised. The training staff member 901 sets the knee extending assistance at a lower level as the desired level of difficulty of the walking training increases. The knee flexing angle is an angle at which knee extending assistance is provided. The knee flexing/extending time is a period during which the knee extending assistance is provided. Further, when this value is large, the knee is assisted so that it is slowly flexed and extended, whereas when this value is small, the knee is assisted so that it is quickly flexed and extended.

The wedge thickness is a height of a member such as a cushion provided in the sole of the shoe of the leg (i.e., the leg on the side on which the walking assistance apparatus 120 is not attached) of the trainee 900 opposite to the paralyzed leg thereof. The weight-off threshold is one of the thresholds for the load applied to the sole. When the load becomes smaller than this threshold, the swinging assistance is cancelled. The load threshold is one of the thresholds for the load applied to the sole. When the load exceeds this threshold, the swinging assist is provided. As described above, the walking assistance apparatus 120 may be configured so that the flexing/extending motion of the knee can be adjusted by four setting parameters, i.e., the knee flexing angle, the knee flexing/extending time, the weight-off threshold, and the load threshold.

Further, the walking training apparatus 100 may also be configured so that setting values of various parameters such as a load and an angle, a target value, a target achievement rate, a target achievement timing, etc. are fed back to the user by a sound output from a speaker(s) (not shown). The above-described setting parameters may include parameters for other settings such as presence/absence of a feedback sound and its volume.

Further, the above-described setting parameters may not be setting parameters directly related to the training. For example, the above-described setting parameters may be setting values for images, music, a type of game, a level of difficulty of game, etc. that are provided through the training monitor 138 or a speaker(s) (not shown) in order to motivate the trainee 900.

Note that the above-described setting parameters are merely examples and other setting parameters may be used. Further, some of the above-described setting parameters may not be used. Further, although the above-described setting parameters include many parameters for adjusting the level of difficulty of the training as described above, they may also include parameters unrelated to the level of difficulty. For example, the walking training apparatus 100 may be configured so as to display an alert icon image that is to be displayed on the training monitor 138. Further, examples of the setting parameters unrelated to the level of difficulty include parameters for increasing the degree of concentration of the trainee 900 on the training, such as the size and the displaying interval of the above-described alert icon image. Further, time information such as date and time at which the parameter setting operation is performed or timing information other than the time (e.g., information indicating a distinction between the stance phase, the swing phase, etc. in one walking cycle) can be added to the above-described setting parameters.

The above-described item (2) is described.

The detection data of the above-described item (2) can be defined as training data of the trainee 900 that is acquired during the rehabilitation in the walking training apparatus 100 together with the data of the above-described item (1).

A typical example of the detection data is sensor data. The sensor data is sensor values detected by various sensors of the walking training apparatus 100. For example, the sensor data includes an inclination angle of the trunk detected by the posture sensor 217, a load and an inclination angle detected by the handrail sensor 218, an angle detected by the angle sensor 223, etc. The sensors that output the sensor data are an acceleration sensor, an angular-speed sensor, a position sensor, an optical sensor, a torque sensor, a load sensor, etc. Further, encoders provided in motors of the winding mechanisms or the like of the front wire 134, the rear wire 136, and the harness wire 111 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 900 by performing image processing based on an image taken by shooting at least an area including the eyes of the trainee 900, or obtained by determining the orientation (upward/downward etc.) of the face of the trainee 900 based on an image taken by shooting at least the face. Such data may also be included in the aforementioned detection data. Further, the detection data may be voice data acquired by a voice acquisition unit, such as a microphone, that acquires a voice of the trainee 900 or the training staff member 901, text data obtained by performing a voice analysis on the voice data, or data obtained by analyzing the text data. The voice of the training staff member 901 may include an encouraging talk to the trainee 900 about, for example, how to correct his/her walking. Further, the sensor data may be data obtained by detecting brain waves of the trainee 900 by using an electroencephalograph, or may be data obtained by detecting brain waves of the training staff member 901 by using an electroencephalograph.

Further, the line-of-sight detection sensor, a shooting unit that takes the above-described image, the microphone, and the like can be disposed in the walking training apparatus 100 itself. Alternatively, they can also be disposed in, for example, an eyeglass-type wearable terminal that is worn by the trainee 900. This terminal may include a wireless communication unit that wirelessly transmits and receives data by a wireless communication technique such as Bluetooth (Registered Trademark). Further, the walking training apparatus 100 may also include a wireless communication unit. In this way, the walking training apparatus 100 can acquire data acquired by the wearable terminal through wireless communication. Although the electroencephalograph is limited to those having a high detection accuracy, it may be disposed in the walking training apparatus 100 itself and configured so that the electroencephalogram of the trainee 900 and that of the training staff member 901 can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as a sensor, is not limited to those described above with reference to FIGS. 1 to 3 or those exemplified by the eyeglass-type wearable terminal. For example, the trainee 900 may wear clothes equipped with a wearable biosensor and/or a wearable touch sensor. Here, the clothes are not limited to those worn on the upper body. That is, they may be those worn on the lower body, a top-and-bottom set, or those attached to a part of the harness 110 or the like. Further, a wireless communication unit like the one described above is provided in each of the clothes and the walking training apparatus 100. In this way, the walking training apparatus 100 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 900, who is the wearer, made from the outside. That is, the wearable touch sensor can acquire data indicating information about a position where the training staff member 901 touched the trainee 900.

Further, the detection data is not limited to the values indicated by the detection signals detected by various sensors and the like. That is, it may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame 122 and the lower-leg frame 123 detected by the angle sensor 223. Further, the sensor data of the angle sensor may include an angular speed that is obtained by differentiating the angle. The sensor data of the acceleration sensor may be a velocity that is obtained by integrating the acceleration or a position that is obtained by integrating the acceleration twice.

For example, the detection data may include the following average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill 131 or a value calculated from the drive signal in the treadmill drive unit 211. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff member 901 has assisted the trainee 900 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times].

Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill 131 that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the pieces of the above-described detection data may not be used. That is, when the detection data is used as rehabilitation data, the server 500 needs to collect at least one piece of detection data.

The above-described item (3) is described. The data related to the trainee 900 (hereinafter referred to as trainee data) indicates, for example, properties of the trainee 900. Examples of the trainee data include the age, the sex, the physique (the height, the weight, etc.) of the trainee 900, information about the symptom, the Br. Stage, the SIAS, the initial walking FIM, and the latest walking FIM. Further, the trainee data may also include the name or the ID of the trainee 900. Further, the trainee data may also include preference information indicating the preference of the trainee 900 and personality information indicating his/her personality. Further, the trainee data may include, as the FIM, an exercise item other than those related to the walking ability, and may include a recognition item. That is, the trainee data may include various kinds of data indicating physical abilities of the trainee 900. Note that part or all of the trainee data may be referred to as body information, basic information, or trainee feature information.

Note that the symptom information may include information indicating an initial symptom, a time when the symptom appears, and a current symptom. Further, it can be considered that the trainee 900 needs to perform rehabilitation mainly because of at least one of the symptoms described above. However, the symptom information may also include symptoms that are unlikely to be directly related to the rehabilitation. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. Stage means a Brunnstrom Recovery Stage in which a recovery process of a hemiplegia is divided into six stages based on the observation. The trainee data may include, of the Br. S stage, lower-limb items that are main items related to the walking training apparatus 100. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one to seven points according to the level of assistance.

For example, a walking FIM is a general index indicating the degree of recovery. Further, the walking FIM is an index indicating the moving ability (i.e., walking ability) of the trainee when no actuator is used. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 900 gradually increases.

Therefore, the walking FIM is used as an index indicating the degree of recovery of the trainee 900 from the start of the rehabilitation. The walking FIM is used as an index indicating the moving ability of the trainee 900 when no actuator is used, i.e., an index indicating his/her walking ability. In other words, the walking FIM is an important index in order to recognize the degree of progress of the rehabilitation of the trainee 900. However, in order to grade the walking FIM, the trainee 900 needs to walk 50 m on a flat ground in a state in which the assistant is present near the trainee 900. Therefore, it is possible that the walking FIM cannot be graded frequently. Further, as described above, only the assistance level is different between the case in which the walking FIM is determined to be three points and the case in which the walking FIM is determined to be four points. That is, the grading of the walking FIM may vary depending on the assistant (training staff member). Note that the walking distance in the evaluation of the walking FIM is not limited to 50 m. For example, the walking distance may be 15 m.

As can be understood from the above description, the latest walking FIM used by the walking training apparatus 100 is used as not only an index indicating the physical ability of the trainee 900 but also an index indicating the degree of recovery of the trainee 900 from the start of the rehabilitation. In other words, the walking FIM is an important index in order to recognize the degree of progress of the rehabilitation of the trainee 900. Further, the amount of change from the initial walking FIM to the latest walking FIM or its changing speed is also used as an index indicating the degree of recovery. The changing speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in a case where the trainee 900 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

As described above, the trainee data in the above-described item (3) may include index data about rehabilitation performed by the trainee 900 by using the walking training apparatus 100, including at least one of the symptom, the physical ability, and the degree of recovery of the trainee 900. Note that in general, data that can be included in both concepts of the physical ability and the degree of recovery, such as the latest walking FIM, may be included in one of them. However, such data can also be included in both of them. Note that the same is applicable to all the items of the rehabilitation data. Further, data of a given item can be handled as data of one or a plurality of the above-described items (1) to (4). Further, time information such as the date and time at which the walking FIM is acquired, e.g., the measurement date of the walking FIM may be added in the above-described trainee data.

The above-described item (4) is described.

The data about the training staff member 901 (hereinafter referred to as staff data) indicates, for example, the property of the training staff member 901. The staff data includes the name or the ID, the age, the sex, the physique (the height, the weight, etc.) of the training staff member 901, the name of the hospital to which the training staff member 901 belongs, and his/her years of experience as a PT or a doctor. The staff data may include, as data related to the assistance, a value that numerically represents the timing at which the trainee 900 is assisted.

Further, in a case where a plurality of training staff members simultaneously assist the rehabilitation, the rehabilitation data may include data of the plurality of staff members. Further, each of the pieces of staff data may include information indicating whether the staff member is the main training staff member, an assistance training staff member, a training staff member who performs only an operation, or a training staff member who just physically supports the trainee 900 by his/her hand.

Further, the walking training apparatus 100 may be configured so that a user can enter a rehabilitation plan for the trainee 900. Further, the data of the rehabilitation plan entered as described above may also be included as staff data related to the training staff member 901 who has entered the data or as rehabilitation data belonging to other categories. Further, the walking training apparatus 100 may be configured so that, to make it possible to cope with the change of the training staff member 901, a user can enter remarks and/or messages for assisting the training of the trainee 900 in the future. Further, the data entered as described above may also be included as staff data related to the training staff member 901 who has entered the data or as rehabilitation data belonging to other categories.

The reason for including these piece of data in the rehabilitation data is that it is possible that a training staff member has been able to successfully carry out the training of the trainee 900 because of the presence of remarks and/or messages given by other skilled training staff members. Further, time information such as the date and time at which the rehabilitation plan is entered, e.g., the input date and time of the rehabilitation plan may be added in the above-described staff data.

(Abnormal Walking Determination in Walking Evaluation Unit 210a)

The walking evaluation unit 210a will be described in detail. The walking evaluation unit 210a evaluates, for each walking cycle, whether the walking motion corresponds to abnormal walking patterns. The present inventors have found that there are at least seven patterns of abnormal walking in hemiplegic patients. That is, in a case where an abnormal walking criterion is set for each pattern, it can be seen that the walking motion can be evaluated as abnormal walking in a case in which the walking of the trainee meets any one of the abnormal walking criteria. In the walking training apparatus 100 according to this embodiment, the walking evaluation unit 210a evaluates whether the walking motion of the trainee is abnormal walking by comparing the motion amount of each paralyzed body part with each of the abnormal walking criteria. Hereinafter, each abnormal walking criterion and an abnormal walking evaluation method will be described.

Figure 5:
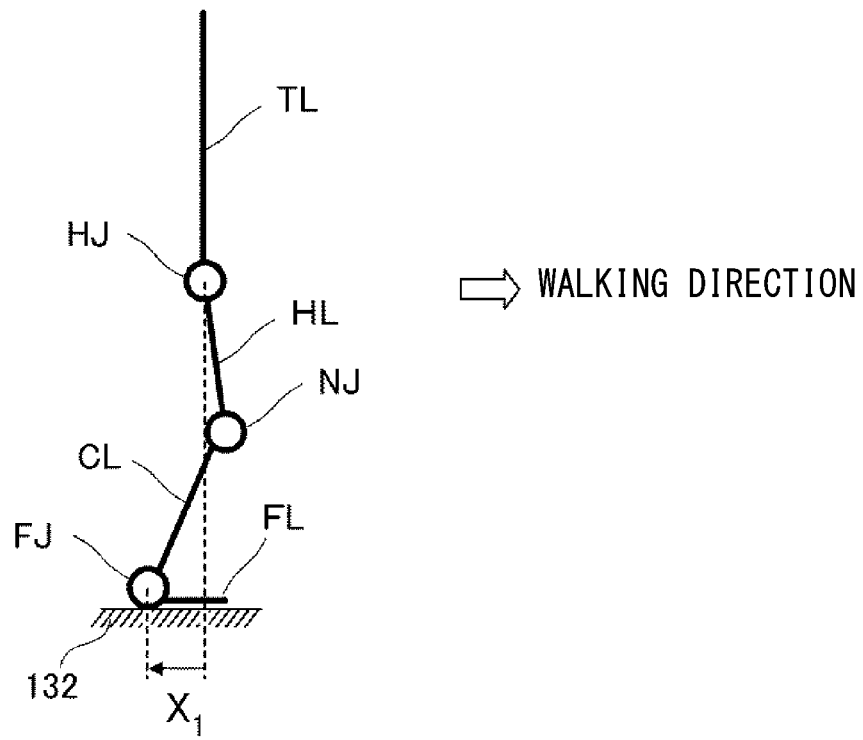
FIG. 5 is a diagram illustrating a first abnormal walking criterion.

FIG. 5 is a diagram illustrating the first abnormal walking criterion. FIG. 5 is a schematic view in a case in which a paralyzed body part, which is the lower body of the diseased leg side, is observed from the side with respect to the walking direction, and shows a trunk TL, a hip joint HJ, an upper leg HL, a knee joint NJ, a lower leg CL, a foot joint FJ, and a foot FL from the top to the bottom. In the present embodiment, a "leg" and a "leg part" are used as terms indicating the entire lower part than the hip joint HJ, and a "foot" and a "foot part" are used as terms indicating parts from the ankle to the toe.

In order to determine whether the walking of the trainee meets the first abnormal walking criterion, the overall control unit 210 detects, as a first motion amount according to the walking motion, a distance $X_1$ along the walking direction from the hip joint HJ to the foot joint FJ in a case in which the diseased leg has finished a swing phase and landed. In the normal walking of a normal leg, the point of landing after the swing phase should be located ahead of the hip joint HJ in the walking direction. However, in the walking of the diseased leg, the diseased leg cannot be sufficiently moved to the front since the diseased leg cannot be sufficiently swung. For this reason, the point of landing may be slightly ahead of the hip joint HJ, or may be behind the hip joint HJ.

"Less than a reference distance $X_{c1}$" is set as the first abnormal walking criterion. In a case in which the distance $X_1$ detected in the walking motion is less than the reference distance $X_{c1}$, this walking is determined to be abnormal walking. The overall control unit 210 acquires the detection signal from the load sensor 222 and the image data from the camera 140, and detects the distance $X_1$ at the end of the swing phase using the acquired information. When, for example, $X_{c1}$=20 cm (20 cm forward the hip joint HJ) is set, the walking evaluation unit 210a evaluates the walking motion of the trainee as abnormal walking in a case in which the detected distance $X_1$ is 10 cm or −5 cm. The reference distance $X_{c1}$ may be changed according to the physique of the trainee, the degree of progress of rehabilitation and the like.

Figure 6:
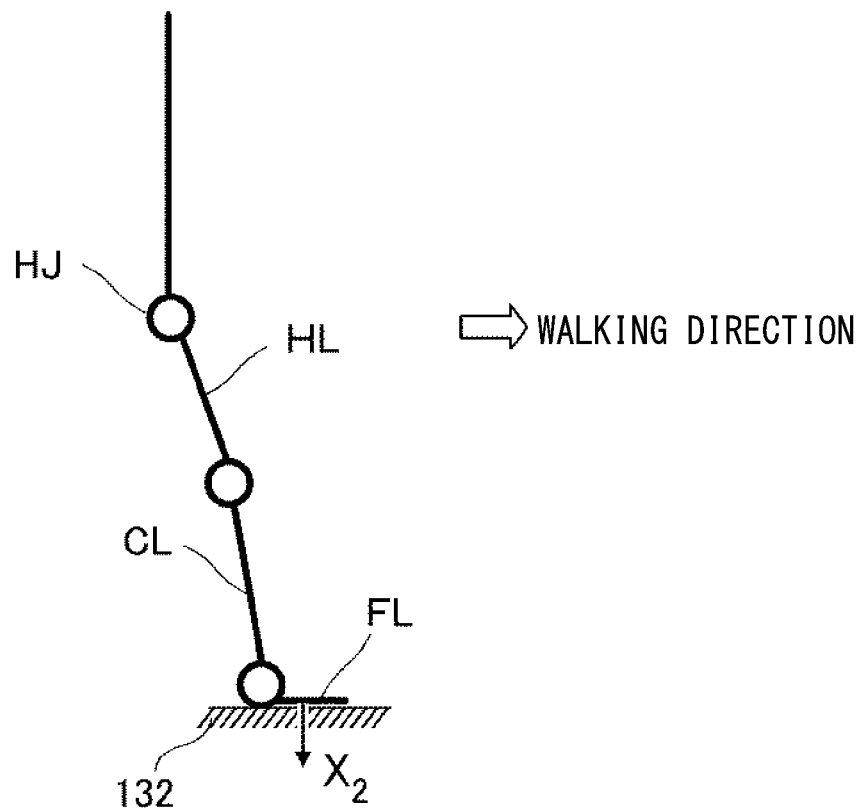
FIG. 6 is a diagram illustrating a second abnormal walking criterion.

FIG. 6 is a diagram illustrating the second abnormal walking criterion. FIG. 6 is a schematic view in a case in which a paralyzed body part, which is the lower body of the diseased leg side, is observed from the side with respect to the walking direction, and shows each body part in the same manner as in FIG. 5.

In order to determine whether the walking of the trainee 900 meets the second abnormal walking criterion, the overall control unit 210 detects a sole load $X_2$ in the swing phase of the diseased leg as a second motion amount according to the walking motion. In the normal walking of a normal leg, the sole does not touch the ground in the swing phase. However, in the walking of the diseased leg, there is not enough power to lift the entire leg. For this reason, so-called dragging walking may occur, such as pushing the leg forward with the sole in contact with the ground.

"Larger than a reference load $X_{c2}$" is set as the second abnormal walking criterion. In a case in which the load $X_2$ detected in the walking motion is larger than the reference load $X_{c2}$, this walking is determined to be abnormal walking. The overall control unit 210 acquires the detection signal from the load sensor 222 and the image data from the camera 140, and detects the load $X_2$ in the swing phase using the acquired information. Normally, $X_{c2}$=0 is set. That is, even when a slight load from the sole is detected in the swing phase, the walking evaluation unit 210a evaluates the walking motion of the trainee as abnormal walking. The walking evaluation unit 210a may allow some ground contact according to the degree of progress of rehabilitation or the like. For example, $X_{c2}$=10N may be set. The walking evaluation unit 210a may use the accumulated load in the swing phase as a reference value.

Figure 7:
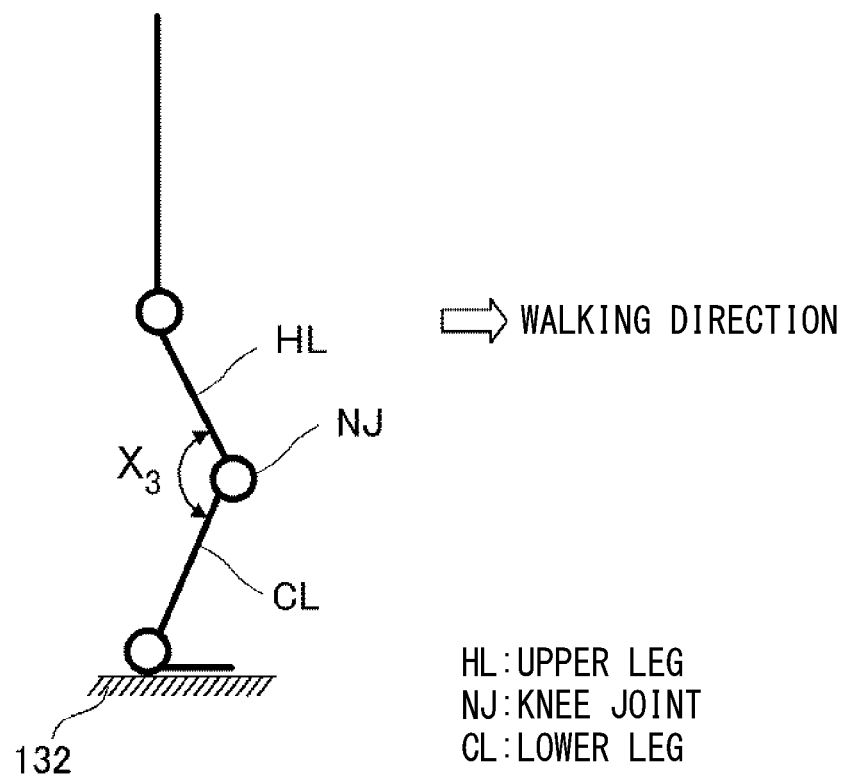
FIG. 7 is a diagram illustrating a third abnormal walking criterion.

FIG. 7 is a diagram illustrating the third abnormal walking criterion. FIG. 7 is a schematic view in a case in which a paralyzed body part, which is the lower body of the diseased leg side, is observed from the side with respect to the walking direction, and shows each body part in the same manner as in FIG. 5.

In order to determine whether the walking of the trainee meets the third abnormal walking criterion, the overall control unit 210 detects a flexing angle $X_3$ of the knee joint NJ during the stance of the diseased leg as a third motion amount according to the walking motion. In the normal walking of a normal leg, the knee joint NJ during the stance does not bend so much. However, in the walking of the diseased leg, the knee joint NJ may bend greatly during the stance since the power of the knee joint NJ to support the upper body is not sufficiently large. In some cases, so-called knee folding occurs.

"Less than a reference angle $X_{c3}$" is set as the third abnormal walking criterion. When the flexing angle $X_3$ detected in the walking motion is smaller than the reference angle $X_{c3}$, this walking is determined to be abnormal walking. The overall control unit 210 acquires the detection signal from the angle sensor 223 and the image data from the camera 140, and detects the flexing angle $X_3$ during the stance using the acquired information. When, for example, $X_{c3}=165$ is set, if the detected flexing angle $X_3$ is 140 degrees, the walking evaluation unit 210a evaluates the walking motion of the trainee as abnormal walking. The walking evaluation unit 210a evaluates that the walking motion of the trainee as abnormal walking in a case in which the flexing angle $X_3$ continuously detected during the stance becomes less than the reference angle $X_{c3}$ at least once. The reference angle $X_{c3}$ may be changed according to the age of the trainee, the degree of progress of rehabilitation and the like.

Figure 8:
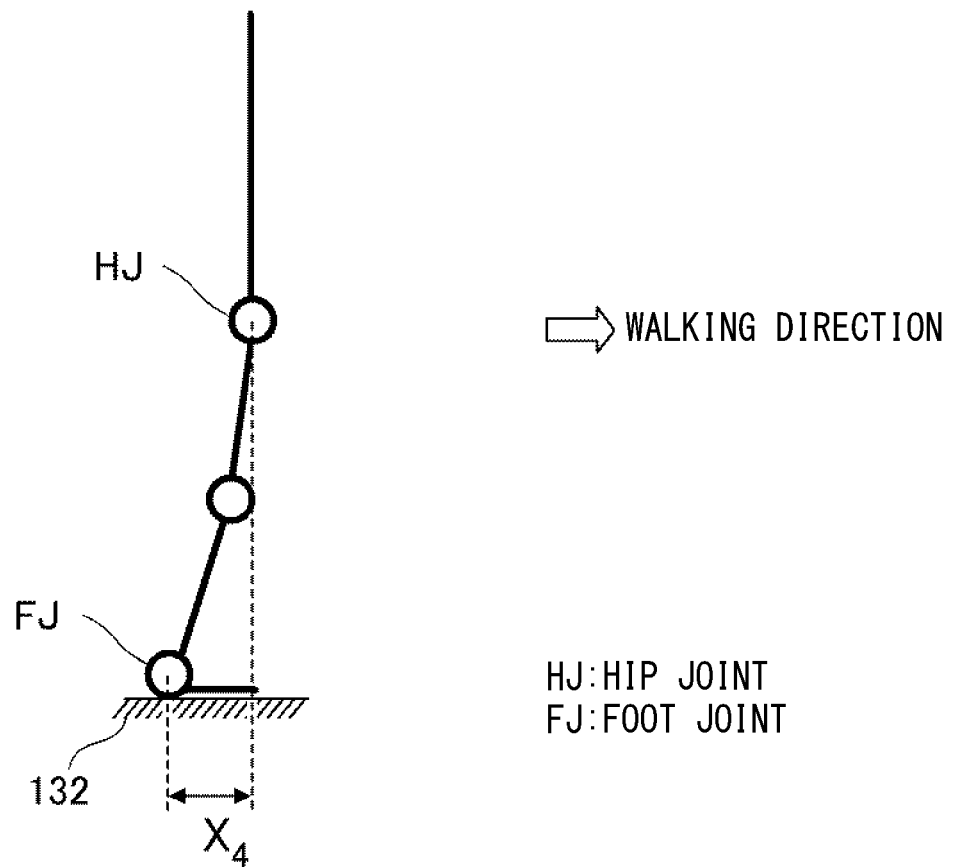
FIG. 8 is a diagram illustrating a fourth abnormal walking criterion.

FIG. 8 is a diagram illustrating the fourth abnormal walking criterion. FIG. 8 is a schematic view in a case in which a paralyzed body part, which is the lower body of the diseased leg side, is observed from the side with respect to the walking direction, and shows each body part in the same manner as in FIG. 5.

In order to determine whether the walking of the trainee meets the fourth abnormal walking criterion, the overall control unit 210 detects, as a fourth motion amount according to the walking motion, a distance $X_4$ along the walking direction from the hip joint HJ to the foot joint FJ at the time of swinging at which the diseased leg switches from the stance phase to the swing phase. In the walking of a healthy person, the foot joint FJ at the time of swinging is located behind the hip joint HJ to some extent. However, in the walking by a patient who suffers from paralysis, since the weight shift of the upper body cannot be freely performed, swinging may be started before the foot joint FJ is sufficiently separated from the hip joint HJ.

"Equal to or greater than a reference distance $X_{c4}$" is set as the fourth abnormal walking criterion. In a case in which the distance $X_4$ detected in the walking motion is less than the reference distance $X_{c4}$, this walking is determined to be abnormal walking. The overall control unit 210 acquires the detection signal from the load sensor 222 and the image data from the camera 140, and detects the distance $X_4$ at the time of swinging at which the diseased leg switches from the stance phase to the swing phase using the acquired information. When, for example, $X_{c4}=-20$ cm (20 cm backward from the hip joint HJ) is set, the walking evaluation unit 210a evaluates the walking motion of the trainee as abnormal walking in a case in which the detected distance $X_4$ is −10 cm (10 cm backward from the hip joint HJ) or 5 cm (=5 cm forward from the hip joint HJ). The reference distance $X_{c4}$ may be changed according to the physique of the trainee, the degree of progress of rehabilitation and the like.

Figure 9:
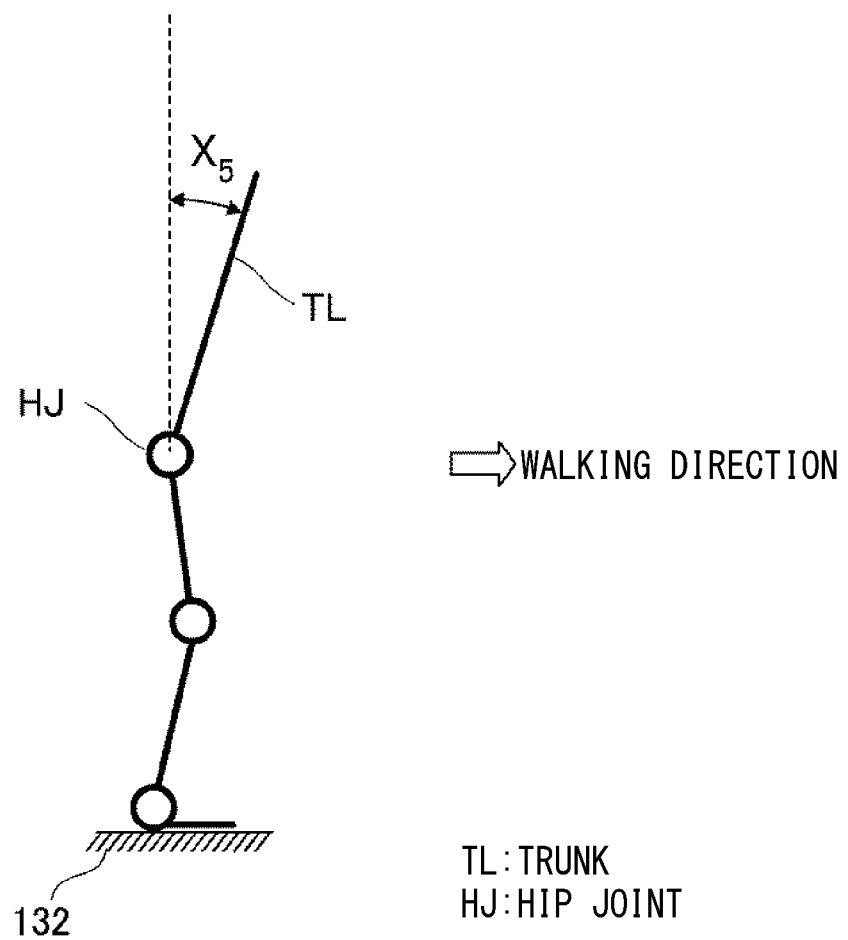
FIG. 9 is a diagram illustrating a fifth abnormal walking criterion.

FIG. 9 is a diagram illustrating the fifth abnormal walking criterion. FIG. 9 is a schematic view in a case in which a paralyzed body part, which is the lower body of the diseased leg side, is observed from the side with respect to the walking direction, and shows each body part in the same manner as in FIG. 5.

In order to determine whether the walking of the trainee meets the fifth abnormal walking criterion, the overall control unit 210 detects an inclination angle $X_5$ of the trunk TL in the forward direction during the stance of the diseased leg as a fifth motion amount according to the walking motion. In the normal walking of a healthy person, the trunk TL during the stance is slightly inclined forward with respect to the vertical line passing through the hip joint HJ. However, in the walking of a patient who suffers from paralysis, in order to try to protect the lower body, the trunk TL may be greatly inclined forward with respect to the vertical line passing through the hip joint HJ.

"Equal to or greater than a reference angle $X_{c5}$" is set as the fifth abnormal walking criterion. In a case in which the inclination angle $X_5$ in the forward direction detected in the walking motion is equal to or greater than the reference angle $X_{c5}$, this walking is determined to be abnormal walking. The overall control unit 210 acquires the detection signal from the posture sensor 217 and the image data from the camera 140, and detects the inclination angle $X_5$ during the stance using the acquired information. When, for example, $X_{c5}=10$ degrees is set, the walking evaluation unit 210a evaluates the walking motion of the trainee as abnormal walking in a case in which the detected inclination angle $X_5$ is 30 degrees. The walking evaluation unit 210a evaluates the walking motion of the trainee as abnormal walking in a case in which the inclination angle $X_5$ continuously detected during the stance becomes equal to or greater than the reference angle $X_{c5}$ at least once. The reference angle $X_{c5}$ may be changed according to the age of the trainee, the degree of progress of rehabilitation and the like.

Figure 10:
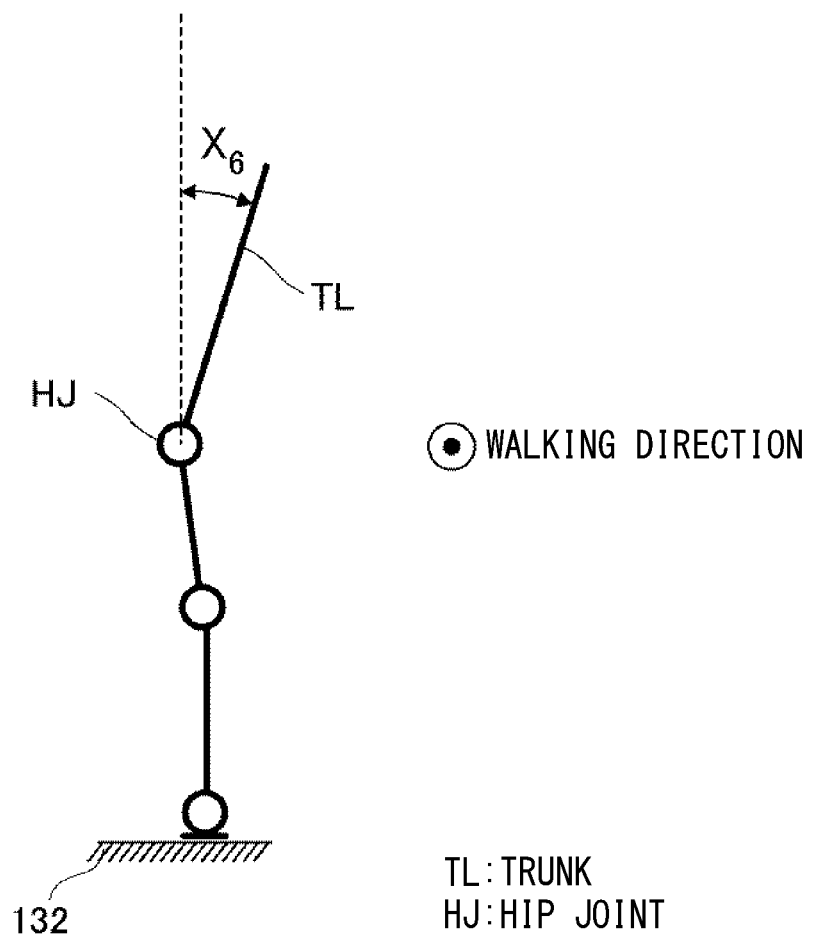
FIG. 10 is a diagram illustrating a sixth abnormal walking criterion.

FIG. 10 is a diagram illustrating the sixth abnormal walking criterion. FIG. 10 is a schematic view in a case in which a paralyzed body part, which is the lower body of the diseased leg side, is observed from the front in the walking direction, and shows each body part in the same manner as in FIG. 5.

In order to determine whether the walking of the trainee meets the sixth abnormal walking criterion, the overall control unit 210 detects an inclination angle $X_6$ of the trunk TL toward the diseased leg side during the stance of the diseased leg as a sixth motion amount according to the walking motion. In the normal walking of a healthy person, the trunk TL during the stance is rarely shaken in the right/left direction with respect to the vertical line passing through the hip joint HJ. However, in the walking of a patient who suffers from paralysis, the trunk TL may be greatly inclined forward toward the diseased leg side with respect to the vertical line passing through the hip joint HJ due to the fear of applying weight to the diseased leg side and the like.

"Equal to or greater than a reference angle $X_{c6}$" is set as the sixth abnormal walking criterion. When the inclination angle $X_6$ toward the diseased leg side detected in the walking motion is equal to or greater than the reference angle $X_{c6}$, this walking is determined to be abnormal walking. The overall control unit 210 acquires the detection signal from the posture sensor 217 and the image data from the camera 140, and detects the inclination angle $X_6$ during the stance using the acquired information. When, for example, $X_{c6}=10$ degrees is set, the walking evaluation unit 210a evaluates the walking motion of the trainee as abnormal walking in a case in which the detected inclination angle $X_6$ is 20 degrees. The walking evaluation unit 210a evaluates the walking motion as abnormal walking when the inclination angle $X_6$ continuously detected during the stance becomes equal to or greater than the reference angle $X_{c6}$ at least once. The reference angle $X_{c6}$ may be changed according to the age of the trainee, the degree of progress of rehabilitation and the like.

Figure 11:
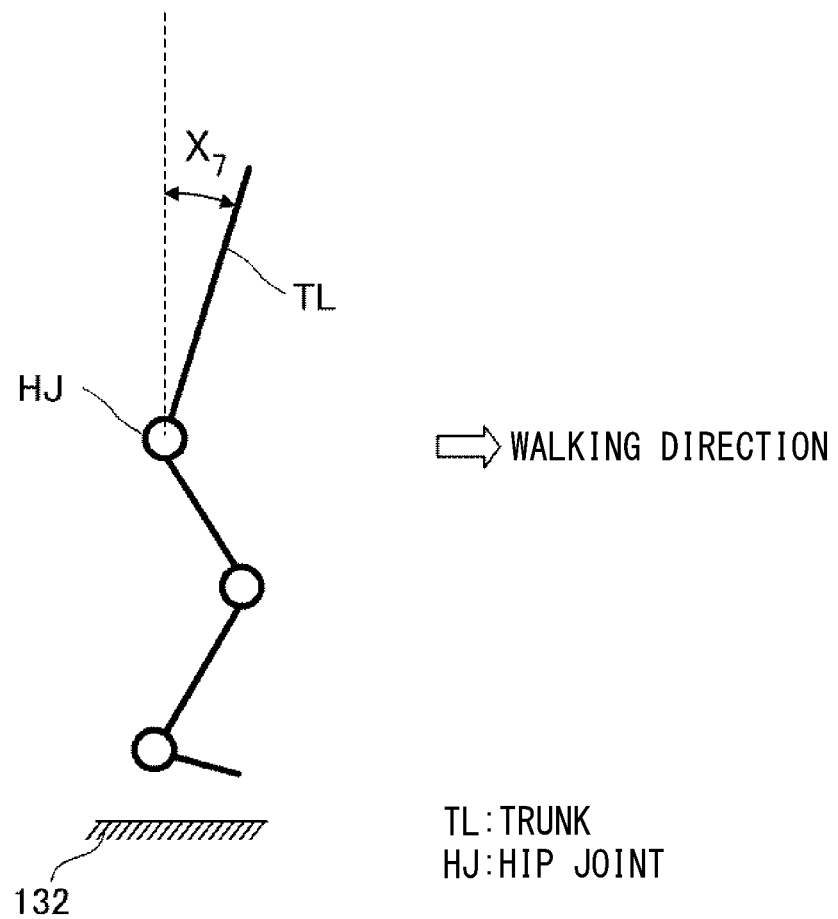
FIG. 11 is a diagram illustrating a seventh abnormal walking criterion.

FIG. 11 is a diagram illustrating the seventh abnormal walking criterion. FIG. 11 is a schematic view in a case in which a paralyzed body part, which is the lower body of the diseased leg side, is observed from the side with respect to the walking direction, and shows each body part in the same manner as in FIG. 5.

In order to determine whether the walking of the trainee meets the seventh abnormal walking criterion, the overall control unit 210 detects an inclination angle $X_7$ of the trunk TL in the forward direction during the swing of the diseased leg as a seventh motion amount according to the walking motion. In the normal walking of a healthy person, the trunk TL during the swing is inclined forward to some extent with respect to the vertical line passing through the hip joint HJ. However, in the walking of a patient who suffers from paralysis, since the weight shift of the upper body cannot be freely performed and accordingly the upper body is bent backward, the trunk TL may be inclined backward with respect to the vertical line passing through the hip joint HJ.

"Less than a reference angle $X_{c7}$" is set as the seventh abnormal walking criterion. When the inclination angle $X_7$ in the forward direction detected in the walking motion is less than the reference angle $X_{c7}$, this walking is determined to be abnormal walking. The overall control unit 210 acquires the detection signal from the posture sensor 217 and the image data from the camera 140, and detects the inclination angle $X_7$ during the swing using the acquired information. When, for example, $X_{c7}=-5$ degrees (=5 degrees backward) is set, the walking evaluation unit 210a evaluates the walking motion of the trainee as abnormal walking in a case in which the detected inclination angle $X_7$ is −20 degrees. The walking evaluation unit 210a evaluates the walking motion as abnormal walking in a case in which the inclination angle $X_7$ continuously detected during the swing becomes less than the reference angle $X_{c7}$ at least once. The reference angle $X_{c7}$ may be changed according to the age of the trainee, the degree of progress of rehabilitation and the like.

While the seven abnormal walking criteria have been described above, other abnormal walking criteria may be added. When abnormal walking criteria are defined, it is needed to define a plurality of abnormal walking criteria, not one abnormal walking criterion. The abnormal walking criteria in this case may include at least two or more abnormal walking criteria relevant to the motion amounts of different parts of the paralyzed body part or at least two or more abnormal walking criteria relevant to the motion amount of the same part of the paralyzed body part in different directions.

Two or more criteria relevant to the motion amounts of different parts may be selected from criteria relevant to the motion amount of the trunk, criteria relevant to the motion amount of the knee joint, and criteria relevant to the motion amount of the foot part from the ankle. In the above examples, the criteria relevant to the motion amount of the trunk are the fifth, sixth, and seventh criteria, the criteria relevant to the motion amount of the knee joint are the third criterion, and the criteria relevant to the motion amount of the foot part are the first, second, and fourth criteria. In a case where a motion amount of interest is selected as described above, it has become obvious through experiments that, in a case where the actual walking should be evaluated as abnormal walking, the actual walking is not evaluated as abnormal walking from one motion amount and is evaluated as abnormal walking from another motion amount in many cases.

Two or more criteria relevant to the motion amount of the same part of the paralyzed body part in different directions may include a criterion relevant to the motion amount of the trunk in the walking direction and a criterion relevant to the motion amount of the trunk in an orthogonal direction perpendicular to the walking direction. In the examples described above, the relationship between any one of the fifth and seventh criteria and the sixth criterion corresponds thereto. Also in a case in which motion amounts of interest are combined as described above, it has become obvious through experiments that, in a case where the actual walking should be evaluated as abnormal walking, the actual walking is not evaluated as abnormal walking from one motion amount and is evaluated as abnormal walking from another motion amount in many cases.

It has been revealed that abnormal walking criteria may be set to different criteria in the swing phase and the stance phase of the diseased leg. The first criterion and the fourth criterion are criteria of the same part in the same direction. However, the first criterion and the fourth criterion are focused on the time point of switching from the swing phase to the stance phase and the time point of switching from the stance phase to the swing phase, respectively. Similarly, the fifth criterion and the seventh criterion are criteria of the same part in the same direction. However, the fifth criterion and the seventh criterion are focused on the stance phase and the swing phase, respectively. Even the motion amounts of the same part in the same direction can be evaluated as different feature amounts of the walking motion in a case where the observation time point can be distinguished.

Figure 12:
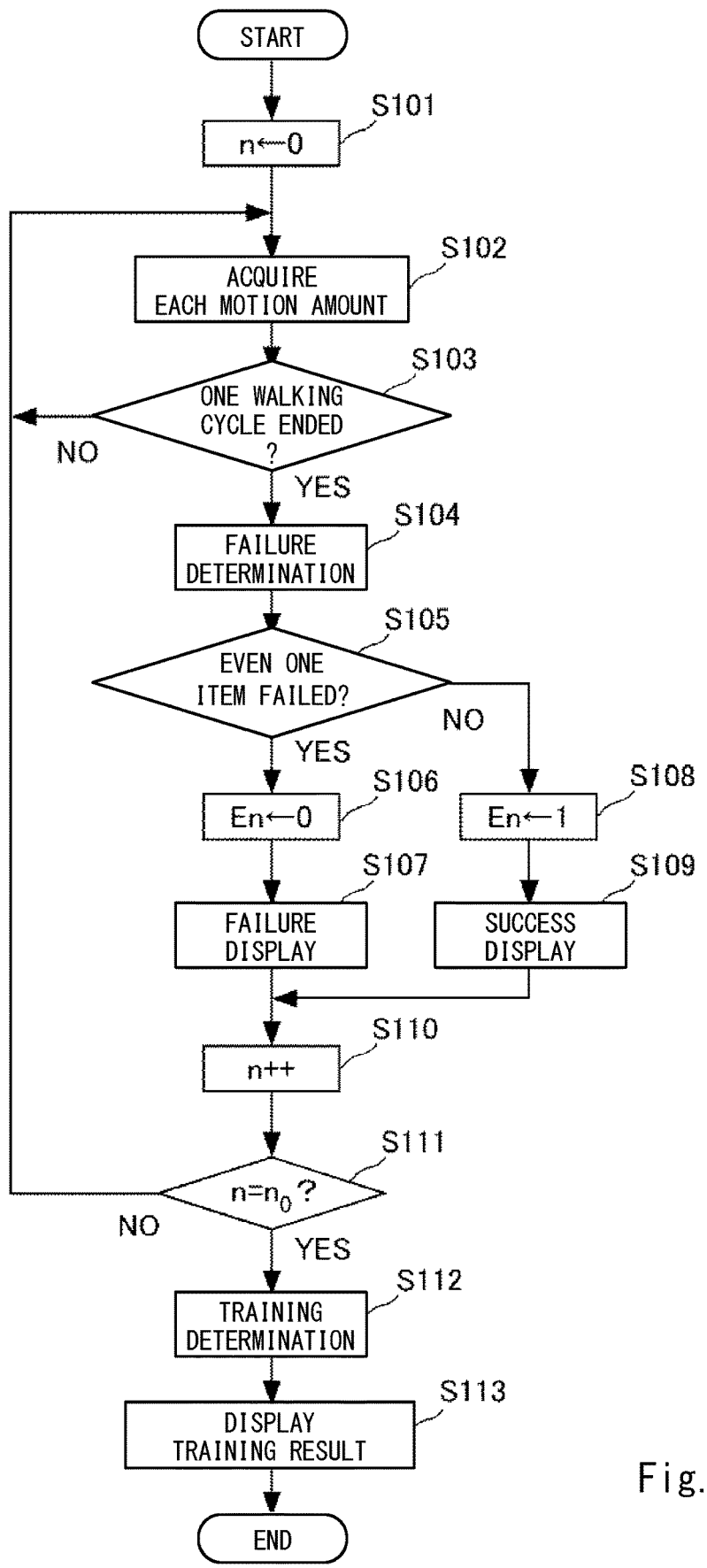
FIG. 12 is a flowchart showing a processing operation of the walking training apparatus.

Next, the processing operation of the walking training apparatus 100 will be described. FIG. 12 is a flowchart showing the processing operation. The flow starts at a point at which a series of training programs are activated in a case in which a training menu is selected by the trainee 900 or the operator.

In Step S101, the overall control unit 210 resets a walking cycle counter n. The overall control unit 210 drives the treadmill drive unit 211 to start the rotation of the belt 132, and drives the pulling drive unit 214 and the joint drive unit 221 according to the set adjustment value, thereby assisting the walking of the trainee 900. In a case where the trainee 900 starts a walking motion, each motion amount according to the walking motion is acquired in Step S102. Specifically, an image processor 216 analyzes the image signal acquired from the camera 140, or the detection signals from the posture sensor 217, the load sensor 222, and the angle sensor 223 are acquired and converted into the motion amount.

In Step S103, the overall control unit 210 determines whether one walking cycle has ended. Evaluation of abnormal walking may be performed for each step of the diseased leg. In this embodiment, however, evaluation is performed in one cycle of one step of the normal leg subsequent to the one step of the diseased leg. Accordingly, in a case where the overall control unit 210 determines that one walking cycle has ended, the process proceeds to Step S104, where the overall control unit 210 executes evaluation. In a case where the overall control unit 210 determines that one walking cycle has not ended, the process returns to Step S102, where the overall control unit 210 continues the acquisition of each motion amount.

In Step S104, the walking evaluation unit 210a of the overall control unit 210 evaluates abnormal walking. Specifically, the walking evaluation unit 210a totals the motion amounts of respective parts in each direction and each period in the walking motion to check whether the totaled amount meets each of the abnormal walking criteria. In a case where the walking motion of the trainee 900 is evaluated as abnormal walking, the walking evaluation unit 210a determines the walking motion as failed walking. In Step S105, the walking evaluation unit 210a determines whether the totaled amount meets one of the abnormal walking criteria described above. In a case where the walking evaluation unit 210a determines that the totaled amount meets one of the abnormal walking criteria described above, the process proceeds to Step S106, where the walking evaluation unit 210a substitutes "0" into an evaluation variable En of the n-th step. Then the overall control unit 210 displays the fact that the one step is failed walking on the training monitor 138 and the management monitor 139 through the display control unit 213. On the other hand, when it is determined in Step S105 that the totaled amount does not meet any one of the abnormal walking criteria described above, the process proceeds to Step S108, where the walking evaluation unit 210a substitutes "1" into the evaluation variable En of the n-th step. The overall control unit 210 displays the fact that the one step is successful walking on the training monitor 138 and the management monitor 139 through the display control unit 213.

In the case of displaying the failed walking in real time during training, the training monitor 138 and the management monitor 139 may perform simple and single display without indicating which one of the abnormal walking criteria the walking motion of the trainee 900 meets. Otherwise, the training monitor 138 and the management monitor 139 may indicate whether the walking motion of the trainee 900 meets each of the abnormal walking criteria. In this case, the evaluation variable En may be prepared for each pattern. Means for presenting whether the walking motion of the trainee 900 is failed walking is not limited to the management monitor 139, and a buzzer sound, blinking light or the like can instead be used. In this case as well, it is desirable to show the sound or the light to the trainee 900 in a simple and single manner. The management monitor 139 for presenting the fact that the walking motion of the trainee 900 is failed walking, a device for generating sound or light and the like function as presentation units for presenting information regarding the evaluation of the walking evaluation unit 210a.

After ending the failure display in Step S107 or the success display in Step S109, the process proceeds to Step S110, where the overall control unit 210 increments the walking cycle counter n. In Step S111, the overall control unit 210 determines whether the walking cycle counter n has reached a walking cycle number no scheduled in a series of walking training programs. In a case where the overall control unit 210 determines that the walking cycle counter n has not yet reached the walking cycle number no, the process goes back to Step S102, where the walking training control is continued. In a case where the overall control unit 210 determines that the walking cycle counter n has reached the walking cycle number no, the process proceeds to Step S112.

In Step S112, the training determination unit 210b of the overall control unit 210 totals the results of the evaluation in a series of walking training trials performed continuously, and performs determination to indicate the success degree of the walking training trial. Specifically, the training determination unit 210b derives a training determination by calculating the ratio of the number of failed walking steps to the total number of walking steps of the diseased leg or by evaluating the number of fall avoiding operations by which the harness drive unit 215 has been operated. The overall control unit 210 ends the series of processing after the training determination unit 210b displays the results of the determination on the training monitor 138 and the management monitor 139 through the display control unit 213 in Step S113.

The walking evaluation unit 210a performs abnormal walking determination based on the predetermined abnormal walking criteria. That is, when the walking motion of the trainee 900 meets one of the abnormal walking criteria, the walking evaluation unit 210a determines that the walking motion of the trainee 900 corresponds to the abnormal walking pattern that meets the abnormal walking criterion. When the walking motion of the trainee 900 does not meet any one of the abnormal walking criteria, the walking evaluation unit 210a determines that the walking motion of the trainee 900 does not correspond to the abnormal walking patterns that meet the abnormal walking criteria. The walking training apparatus 100 records the results of the determination regarding whether the walking motion of the trainee 900 corresponds to the abnormal walking patterns as the detection data.

FIG. 13 is a table illustrating the results of the determination of abnormal walking patterns. As shown in FIG. 13, the detection data includes, for each step, the results of the determination indicating whether the walking motion of the trainee 900 corresponds to seven abnormal walking patterns. In FIG. 13, when the walking motion of the trainee 900 meets an abnormal walking criterion, it is determined to be NG, which indicates that the walking motion of the trainee 900 corresponds to the abnormal walking pattern. On the other hand, when the walking motion of the trainee 900 does not meet an abnormal walking criterion, it is determined to be OK, which indicates that the walking motion of the trainee 900 does not correspond to the abnormal walking pattern. As a matter of course, it is possible that one step may correspond to two or more abnormal walking patterns. While the number of patterns of the abnormal walking is set to be seven in the aforementioned description, it may be smaller than seven or may be eight or more. That is, the number of patterns of abnormal walking may be any number that is equal to or larger than one. The walking training apparatus 100 may store, for each step, the results of the determination in association with moving images in which the walking motion is captured.

The walking training apparatus 100 transmits the results of the determination indicating whether the walking motion of the trainee 900 corresponds to the abnormal walking patterns as shown in FIG. 13 to the server 500 as detection data. The server 500 collects the results of the determination indicating whether the walking motion of the trainee 900 corresponds to the abnormal walking pattern as a part of the rehabilitation data. The walking training apparatus 100 is not limited to have a configuration in which it transmits the results of the determination as the detection data, and may transmit data for determination (e.g., the distance $X_1$). Then the server 500 may perform abnormal walking determination.

(Construction of Learning Model)

Referring is made once again to FIG. 4. The server 500 functions as a learning model construction apparatus that generates a learning model. Specifically, the server 500 collects the rehabilitation data from a plurality of walking training apparatuses 100. Then the server 500 accumulates the collected rehabilitation data in the data accumulation unit 520. The server 500 performs machine learning based on the rehabilitation data, thereby constructing the trained model.

As shown in FIG. 4, the control unit 510 of the server 500 includes a data generation unit 510a and a learning unit 510b. The control unit 510 performs control to machine learn the association between the abnormal walking pattern and the setting parameter. The control unit 510 performs machine learning using the results of the determination of abnormal walking. Specifically, the data generation unit 510a generates a data set before and after the timing when the results of the determination of abnormal walking determination is changed. The learning unit 510b performs machine learning by the RNN using the data set before and after the change in the results of the determination.

Figure 14:
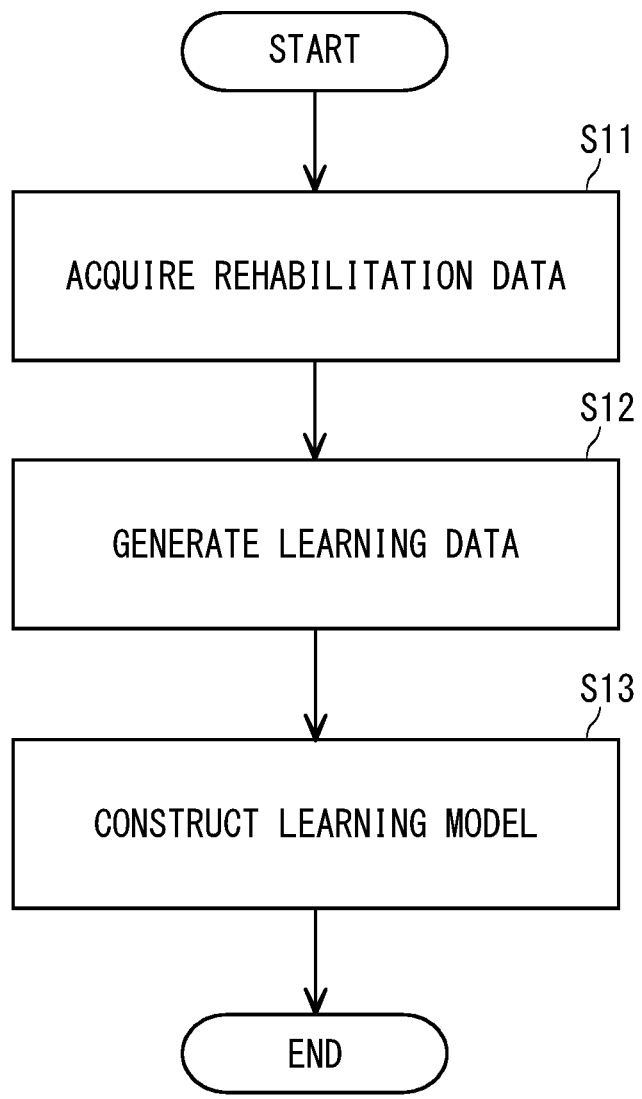
FIG. 14 is a flowchart for explaining processing in a control unit.

FIG. 14 is a flowchart showing a construction method (learning method) of the learning model in the control unit 510. The control unit 510 acquires the rehabilitation data transmitted from the walking training apparatus 100 (S11). The data generation unit 510a generates the learning data as preliminary processing of machine learning (S12). That is, the data generation unit 510a generates the learning data based on the rehabilitation data accumulated in the data accumulation unit 520. The learning unit 510b performs machine learning using the learning data, thereby constructing the learning model (S13).

In the following description, the learning data will be described. In the following description, an amount of movement for determining whether the walking motion of the trainee 900 corresponds to an abnormal walking pattern is referred to as a determination value. Specifically, in the case of the aforementioned seven patterns, the distance $X_1$, the load $X_2$, the flexing angle $X_3$, the distance $X_4$, the inclination angle $X_5$, the inclination angle $X_6$, and the inclination angle $X_7$ are determination values. The amount of movement is a value that can be obtained directly or indirectly from the detection data obtained by various types of sensors. Therefore, the detection data may include the determination values. Note that all the determination values may be normalized so that they are indicated in a fixed range like 0-100%.

Further, a value that serves as a criterion regarding whether the determination value meets the abnormal walking criterion is referred to as a reference value. Specifically, in the case of the aforementioned seven patterns, the reference distance $X_{c1}$, the reference load $X_{c2}$, the reference angle $X_{c3}$, the reference distance $X_{c4}$, the reference angle $X_{c5}$, the reference angle $X_{c6}$, and the reference angle $X_{c7}$ are reference values. The reference values are determination thresholds for determining abnormal walking. The reference values are set by the training staff member 901 of the walking training apparatus 100, a manufacturer, a maintenance operator of the walking training apparatus or the like. Alternatively, a more appropriate reference value or determination threshold may be obtained by machine learning or the like. Further, when the determination value is normalized to 0-100%, the reference value may be a fixed value like 80%.

The walking evaluation unit 210a compares the determination value with the reference value and determines whether the walking motion of the trainee 900 corresponds to abnormal walking. The results of the determination of the respective abnormal walking patterns can be indicated by one-bit data. When, for example, the walking motion of the trainee 900 corresponds to abnormal walking, the result shows "1", whereas when the walking motion of the trainee 900 does not correspond to abnormal walking, the result shows "0". When there are seven abnormal walking patterns, the results of the determination are indicated by 7-bit data. For each walking cycle, 7-bit data indicating the results of determination of abnormal walking is generated.

The data to be used for the abnormal walking determination is referred to as determination data. The determination data is data that can be obtained from the detection data in accordance with the results of the detection in the sensor. The determination data may be included in the detection data. The determination data may be one-bit data indicating the results of the determination or may be data of the reference value. The data accumulation unit 520 accumulates the determination data. The determination data may be included in the rehabilitation data collected from a plurality of walking training apparatuses 100, or may be generated by the server 500 performing operation processing on the rehabilitation data.

The data generation unit 510a prepares a learning data in which the determination data and the setting parameter are associated with each other. That is, the data generation unit 510a associates the determination data with the setting parameter when this determination data is obtained, thereby obtaining one set of learning data. The data generation unit 510a generates data before and after the change in the results of abnormal walking as the learning data.

For example, according to the results of the determination shown in FIG. 13, it is determined that there is no walking abnormality in the first and second steps, the third step corresponds to the walking abnormal pattern 1, and there is no walking abnormality in the fourth to seventh steps. Further, in the eighth and ninth steps, the walking abnormal patterns 2 and 7 occur, which are the same. Therefore, the data generation unit 510a uses each of the data in the second step, that in the third step, that in the fourth step, that in the seventh step, and that in the eighth step as one data set. In other words, since there is no walking abnormality in the fourth to the seventh steps without any changes, the data generation unit 510a excludes the data in the fifth and the sixth steps from the learning data set. According to the above configuration, it is possible to prepare a data set in which there is a great change. Further, since it is possible to eliminate a data set in which there is a small change, it is possible to reduce the load of calculation processing.

Not only in a case in which there is a change in the results of the determination, the data generation unit 510a may generate the data set before and after there is a change in a setting parameter. When, for example, the training staff member 901 has changed the setting parameter such as the assist level in the walking training apparatus 100 during the training of one practice, the overall control unit 210 records the change in the setting parameter for each step. For example, as shown in FIG. 15, the overall control unit 210 may record the value of the setting parameter for each step.

The setting parameters 1-N are parameters that are different from one another. For example, the setting parameter 1 is a treadmill speed [km/h] and the setting parameter 2 is a partial weight-supported amount [%], etc. The walking training apparatus 100 transmits the setting value of the setting parameter for each step to the server 500. The server 500 generates the data set before and after a setting parameter is changed, similar to a case of the results of the determination of the setting parameters.

The data generation unit 510a generates the data set as shown in FIG. 16 as the learning data. FIG. 16 is a table illustrating the learning data sets. One data set includes setting parameter and the determination data. In FIG. 16, the determination data and the setting parameter are associated with each other, thereby forming one data set. Further, one data set may include the trainee data. Further, the data set may include staff data, although it is not shown in the drawings. One data set is data for one walking cycle.

While each of the setting parameter, the determination data, and the trainee data is indicated as one piece of data (e.g., parameter_1) for the sake of simplification of the description in FIG. 16, each of them may actually include a plurality of pieces of data. As described above, the setting parameters may include, for example, two or more pieces of data such as the partial weight-supported amount, the vertical positions of the handrails 130a and the like. As described above, the trainee data may include two or more pieces of data such as the initial walking FIM, the sex, the age and the like of the trainee 900. The trainee data may include the physical features of the trainee such has the height and the weight. The trainee data may include data indicating the degree of recovery or walking ability of the trainee such as the walking FIM.

The determination data is data that can be used for abnormal walking determination. The determination data may be data indicating the results of the determination or may be a determination value. As described above, the determination data differ from each other between two consecutive data sets. Alternatively, the setting parameters differ from each other in two consecutive data sets.

The data generation unit 510a prepares a plurality of sets of the learning data. For example, the rehabilitation data collected in one walking training or one practice of walking training may be prepared as the learning data. Note that one walking training session is a series of trainings performed by one trainee 900. After one walking training session is completed, the next trainee 900 performs training in the walking training apparatus 100. One walking training session usually takes about 20 to 60 minutes. One practice of walking training is one unit during which the trainee 900 continuously walks, included in one walking training session. One walking training session includes a plurality of walking training practices. For example, one practice takes about five minutes. Specifically, in one walking training session, the trainee 900 takes a five-minute break after he/she performs walking training for five minutes. That is, a walking training practice and a break are alternately repeated in one walking training session. The five-minute interval between breaks is the time for one practice. Needless to say, neither the time for one training session nor the time for one practice is limited to any particular time period. That is, they may be set as appropriate for each trainee 900.

The learning unit 510b machine-learns association between the determination data and the setting parameter. That is, the learning unit 510b determines, for each of the abnormal walking patterns, with which one of the setting parameters each of the abnormal walking patterns is strongly associated. Then the learning unit 510b constructs the learning model that receives an abnormal walking pattern and outputs the setting parameter that is strongly associated with this abnormal walking pattern.

For example, the learning unit 510b can perform machine learning as a regression problem that obtains one of a plurality of setting parameters that is strongly associated with the determination data. For example, similarities or a correlation coefficient between the setting parameter and the determination data are obtained for each of the abnormal walking patterns, whereby the associated setting parameter can be obtained. Further, the learning unit 510b may obtain the setting parameter that is strongly associated with the determination data using the concurrence probability that the change in the setting parameter and the change in the results of the determination of the abnormal walking pattern concurrently occur.

The setting parameter that is strongly associated with the determination data is referred to as an associated setting parameter. That is, the associated setting parameter is one of the plurality of setting parameters that has the largest influence on the determination data. The associated setting parameter is a setting parameter for improving the abnormal walking. When, for example, the training staff member 901 changes the setting value of the associated setting parameter, it is highly likely that the results of the determination of the abnormal walking pattern that corresponds to the associated setting parameter may be changed.

Note that the number of associated setting parameters set for one abnormal walking pattern is not limited to one and may be two or larger. In other words, when two setting parameters are changed at the same time, the abnormal walking may be improved. The learning unit 510b obtains one or more associated setting parameters for each of the abnormal walking patterns.

Figure 17:
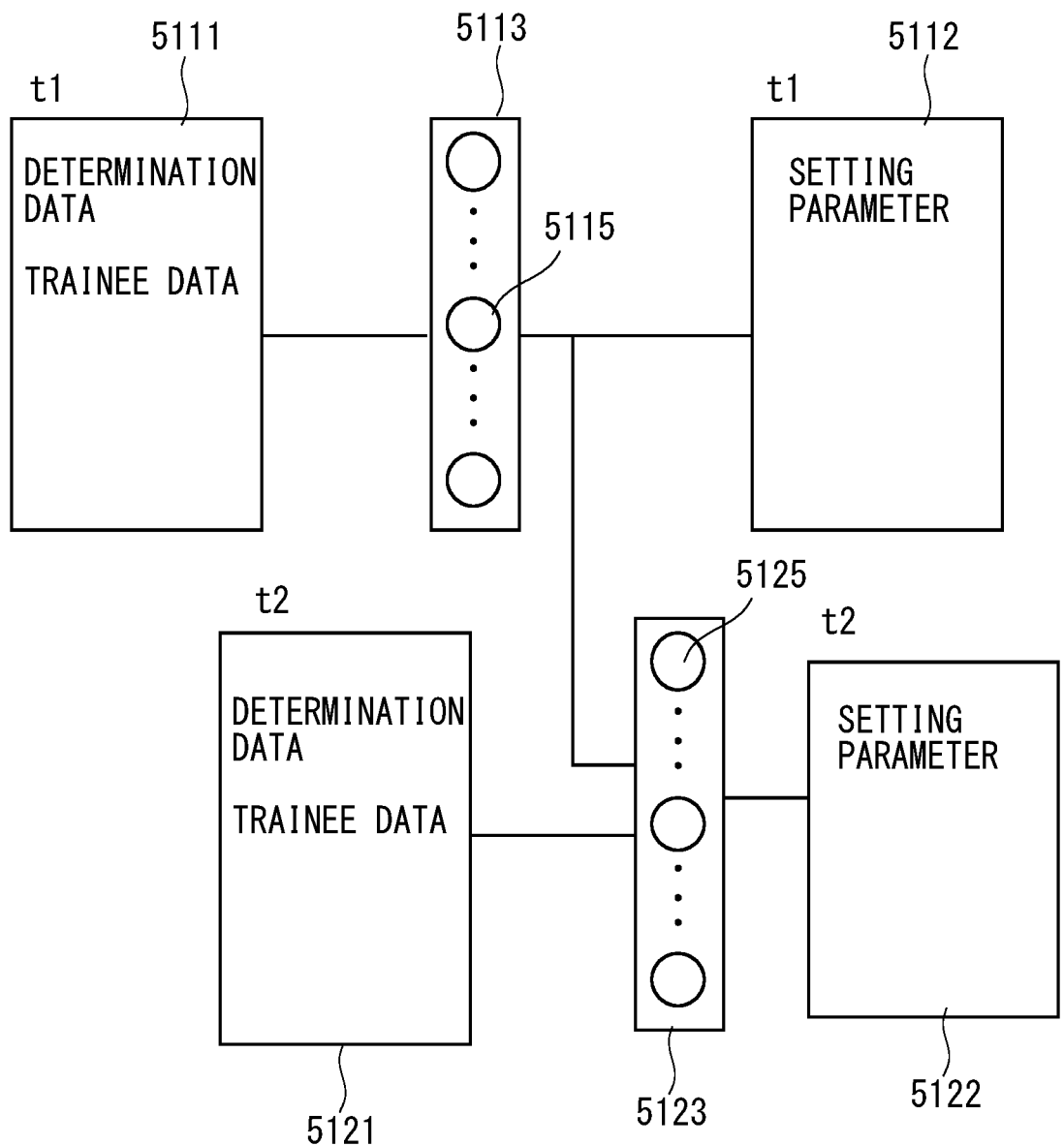
FIG. 17 is a diagram for explaining a learning model.

FIG. 17 is a diagram showing one example of the learning model that the learning unit 510b constructs. FIG. 17 illustrates an example in which the machine learning by the RNN is used. The learning model 5110 includes input layers 5111 and 5121, output layers 5112 and 5122, and intermediate layers (they are also referred to as hidden layers) 5113 and 5123. The input layers 5111 and 5121 receive the determination data and the trainee data. The output layers 5112 and 5122 output the setting parameters.

The input layer 5111 and the output layer 5112 correspond to the data before the change in the results of determination of abnormal walking and the input layer 5121 and the output layer 5122 correspond to the data after the change in the results of determination of abnormal walking. The first one of the two consecutive walking cycles is referred to as a walking cycle t1 and the second one of them is referred to as a walking cycle t2. The input layer 5111 and the output layer 5112 are data at the walking cycle t1 and they are defined as a data set of the first set. The input layer 5121 and the output layer 5122 are data at the walking cycle t2 and they are defined as a data set of the second set.

The intermediate layer 5113 is provided between the input layer 5111 and the output layer 5112. The input layer 5111 receives respective pieces of data included in the data set of the first set. The output layer 5112 outputs setting parameters. The intermediate layer 5113 includes a plurality of nodes 5115. Each of the nodes 5115 includes an activation function. While the intermediate layer 5113 is formed of one layer in FIG. 17, it may be formed of a plurality of layers. In this case, the edges that connect the respective nodes are weighted.

The intermediate layer 5123 is provided between the input layer 5121 and the output layer 5122. The input layer 5121 receives respective pieces of data included in the data set of the second set. The output layer 5122 outputs setting parameters. The intermediate layer 5123 includes a plurality of nodes 5125. Each of the nodes 5125 includes an activation function. While the intermediate layer 5123 is formed of one layer in FIG. 17, it may be formed of a plurality of layers. In this case, the edges that connect the respective nodes are weighted.

Further, the intermediate layer 5113 is coupled to the input side of the intermediate layer 5123. That is, a part or all of the data calculated in the intermediate layer 5113 is input to the intermediate layer 5123. The intermediate layer 5123 receives the output data of the intermediate layer 5113, the determination data of the walking cycle t2 and the like, and outputs the setting parameters of the walking cycle t2.

The learning unit 510b is able to perform supervised learning using the setting parameter as teacher data (correct-answer label). The learning unit 510b constructs the learning model 5110 in such a way that the outputs of the output layers 5112 and 5122 match the actual setting parameter. The learning unit 510b causes the untrained model to read a large number of pieces of learning data in such a way that the error between the value of the actual setting parameter and the output value of the learning model is minimized. The control unit 510 writes the constructed learning model 5110 in the model storage unit 521. The learning model 5110 is a model that uses the setting parameters as objective variables and the determination data and the like as explanatory variables.

While the type and the algorithm of the learning model 5110 learned by the learning unit 510b are not particularly limited, a neural network can be used as the algorithm. In particular, a deep neural network (DNN) using multiple intermediate layers 5113 and 5123 may be used. As the DNN, for example, a feedforward (forward propagation type) neural network such as a multilayer perceptron (MLP) employing an error back propagation method can be used. Further, the learning model 5110 may be a support vector machine (SVM).

The learning unit 510b may construct the learning model by deep learning. The learning unit 510b may construct the learning model by a CNN (Convolutional Neural Network) that performs a convolution operation. In this case, the learning model 5110 may include a convolution layer, a pooling layer and the like. The learning unit 510b may construct the learning model by an RNN (Recurrent Neural Network), LSTM (Long Short Term Memory) or the like that deals with time-series data. In the RNN or the like, the intermediate layer 5113 at the walking cycle t1 is coupled to the intermediate layer 5123 at the walking cycle t2. For example, the rehabilitation data collected at the walking cycle before the change in the results of the determination is used as the learning data set at the walking cycle t1, and the rehabilitation data collected after the change is used as the learning data set at the walking cycle t2.

The data generation unit 510a generates each of the pieces of the rehabilitation data in the walking cycle before and after the change in the results of the evaluation for the abnormal walking pattern as the learning data. The learning unit 510b sequentially inputs the rehabilitation data in the walking cycle before and after the change in the results of the evaluation as one data set, thereby performing machine learning. The learning unit 510b constructs the learning model that receives the abnormal walking pattern and outputs the setting parameter.

In order to sequentially input the input data at each time in one practice or at one walking cycle, one data set may include time-series data such as the detection data. When, for example, the data of a torque sensor or the like is changed in accordance with the timing at one walking cycle, one data set includes time-series detection data. That is, the learning data set may include time-series log data of the detection data. The feature values extracted from the log data may be used as the learning data.

Further, when two or more setting parameters are changed at the same time, it is difficult to determine which one of the setting parameters greatly contributes to improvement in the abnormal walking pattern. Therefore, when two or more setting parameters are changed at the same time, these two or more setting parameters that have been concurrently changed may be weighted. That is, the learning unit 510b may weight the setting parameters. It is therefore possible to perform learning more appropriately.

As described above, the untrained model includes not only a completely untrained model but also a model under a learning process. Note that since a publicly-known algorithm can be used for the learning method used by the learning unit 510b, detailed descriptions thereof will be omitted.

The learning unit 510b is able to construct the learning model that receives the determination data and outputs the setting parameter. Further, the learning unit 510b constructs the learning model using the actual setting parameter as the teacher data. Accordingly, the learning unit 510b is able to construct an appropriate learning model. After the machine learning is completed, the learning unit 510b writes the learning model 5110 in the model storage unit 521.

In the following description, the learning model that has been written in the model storage unit 521 after the completion of the machine learning is also referred to as a trained model. That is, the learning model at a usage stage is also referred to as a trained model. As a matter of course, when new rehabilitation data is accumulated in the data accumulation unit 520, additional machine learning may be performed and the trained model may be updated.

Figure 18:
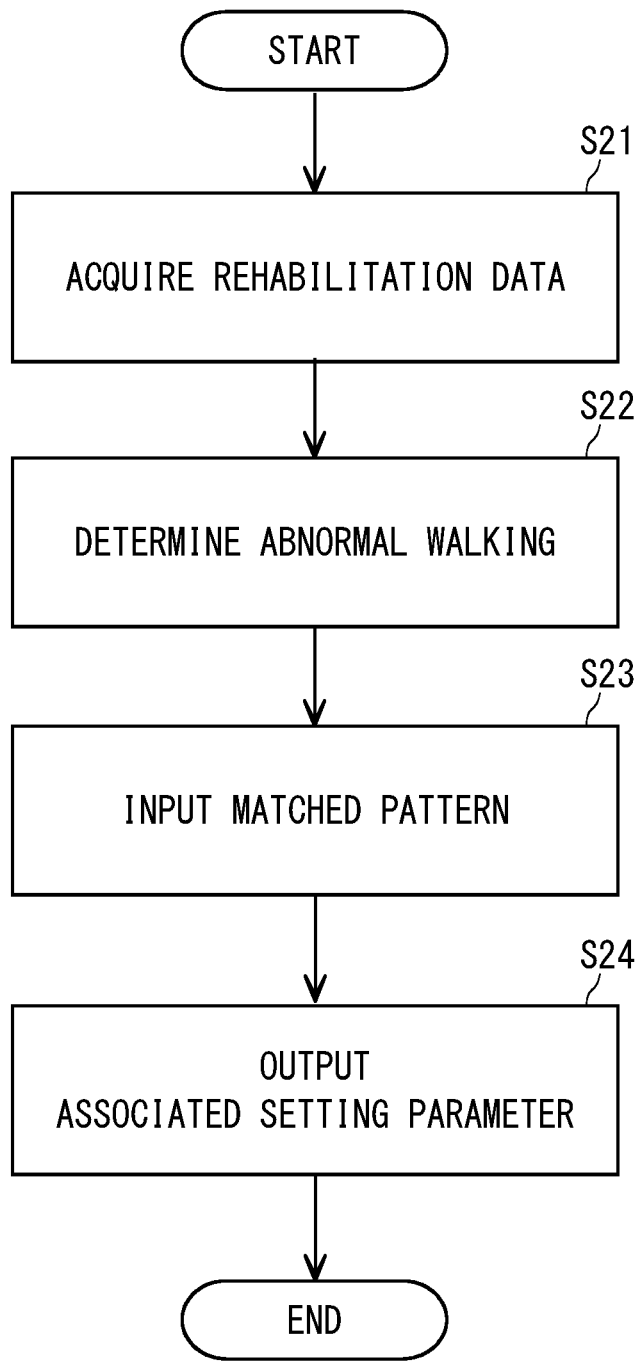
FIG. 18 is a flowchart illustrating an operation method of the walking training apparatus using a learning model.

The control unit 510 or the walking training apparatus 100 outputs the setting parameter from newly-collected rehabilitation data using the trained model. In the following description, with reference to FIG. 18, usage of the trained model will be described. FIG. 18 is a flowchart showing processing that uses the trained model. It is assumed here that the overall control unit 210 of the walking training apparatus 100 uses the trained model. Note that the rehabilitation data that has been newly collected is also referred to as rehabilitation data for evaluation.

When the new trainee 900 performs walking training, the walking training apparatus 100 acquires rehabilitation data (S21). The walking evaluation unit 210a performs the abnormal walking determination based on the detection data of the rehabilitation data (S22). That is, the walking evaluation unit 210a determines whether each of the abnormal walking patterns matches the abnormal walking criteria. Specifically, the walking evaluation unit 210a obtains the determination value of the abnormal walking pattern and compares the determination value with the reference value. The walking evaluation unit 210a outputs the results of the determination for each of the abnormal walking patterns. In the following description, the abnormal walking pattern that matches a criterion is referred to as a matched pattern.

Then the overall control unit 210 inputs the matched pattern in the trained model (S23). Then the overall control unit 210 outputs the associated setting parameter associated with the matched pattern (S24). For example, the notification control unit 210d causes the management monitor 139 to display the associated setting parameter. Accordingly, the management monitor 139 can present the associated setting parameter for the training staff member 901. The training staff member 901 adjusts the associated setting parameter that has been presented.

Figure 19:
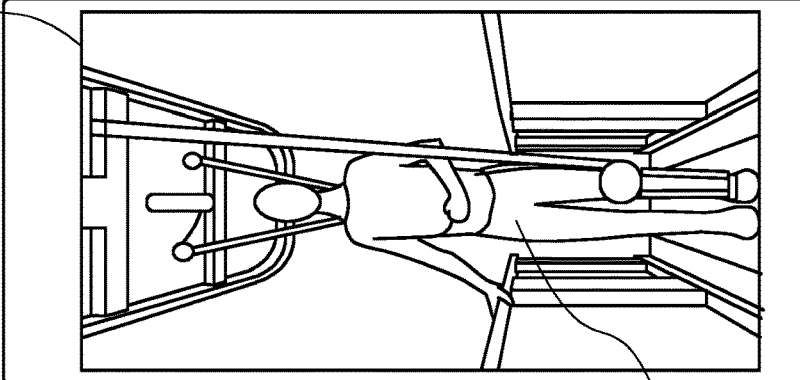
FIG. 19 is a diagram showing a monitor screen that presents associated setting parameters.

FIG. 19 is a diagram showing one example of the display screen of the management monitor 139. The display screen 139a includes a camera image screen 139b, an abnormal walking pattern table 139c, and a setting parameter table 139d.

The camera image screen 139b displays images captured by the camera 140 in real time. FIG. 19 shows an example in which the camera 140 captures images of the trainee 900 from a front side. The camera image screen 139b displays the walking motion of the trainee 900. The training staff member 901 is able to visually recognize the walking motion of the trainee 900.

The abnormal walking pattern table 139c shows, for each of the abnormal walking patterns, the result of the evaluation. The abnormal walking pattern table 139c shows the seven abnormal walking patterns from patterns 1-7. Further, the pattern 5 is the matched pattern 139e that matches the abnormal walking criterion.

The setting parameter table 139d displays a plurality of setting parameters. In this example, the associated setting parameter 139f that corresponds to the matched pattern 139e is a swinging assistance amount. The associated setting parameter 139f is highlighted by a thick frame. Accordingly, the training staff member 901 can promptly recognize the setting parameter whose setting should be changed.

Further, the setting parameter table 139d shows the adjustment direction of the associated setting parameter 139f. This table shows that the abnormal walking is improved by increasing the swinging assistance amount, which is the associated setting parameter 139f. That is, the adjustment direction shows the direction for improving the abnormal walking regarding the setting parameter. The setting parameter table 139d shows whether the adjustment direction for improving the abnormal walking is a direction in which the setting parameter is increased (UP) or decreased (Down). The adjustment direction is not limited to the increase/decrease direction and may be the front/back direction or the right/left direction.

The training staff member 901 checks the setting parameter table 139d and changes the setting value of the associated setting parameter. It is therefore possible to improve the abnormal walking. That is, the training staff member 901 can appropriately set the training setting parameter, whereby the actuator, which is a factor of abnormal walking, operates appropriately. Since the actuator is operated at an appropriate setting parameter, the cases in which the walking motion of the trainee 900 is determined to be abnormal walking can be reduced.

For example, the training staff member 901 who has seen the display screen 139a shown in FIG. 19 increases the swinging assistance amount by one level. The abnormal walking of the pattern 5 that matches an abnormal walking criterion can be promptly improved. That is, since the actuator is operated in accordance with the setting parameter after the adjustment, the actuator is able to appropriately assist the walking motion. By changing the associated setting parameter, the assisting amount becomes an appropriate one. The trainee 900 can perform walking training with a walking motion that does not result in abnormal walking, whereby the trainee 900 can perform walking training more appropriately.

While the associated setting parameter 139f is presented for the training staff member 901 by displaying it by a thick frame in FIG. 19, it may be presented by other methods. In the display screen 139a, for example, the associated setting parameter 139f may be highlighted by blinking the associated setting parameter 139f or changing the display color. Alternatively, the associated setting parameter may be presented by a sound output using a speaker. Otherwise, the management monitor 139 may display a pop-up window showing a message asking the training staff member 901 whether to change the associated setting parameter 139f.

When there are two patterns that match the abnormal walking criteria at the same time, the overall control unit 210 may present the associated setting parameter for each of them. Further, the associated setting parameter may be independently set for each of the abnormal walking patterns. Alternatively, when the walking motion corresponds to two or more abnormal walking patterns at the same time, the associated setting parameter may be set for each of the combinations of the abnormal walking patterns.

Modified Example

In a modified example, the abnormal walking determination is different from that described in the first embodiment. Specifically, shortly after a change in the setting value of the setting parameter, it is determined whether the walking motion of the trainee 900 matches the abnormal walking criteria using an average value of motion amounts for a plurality of walking cycles.

Figure 20:
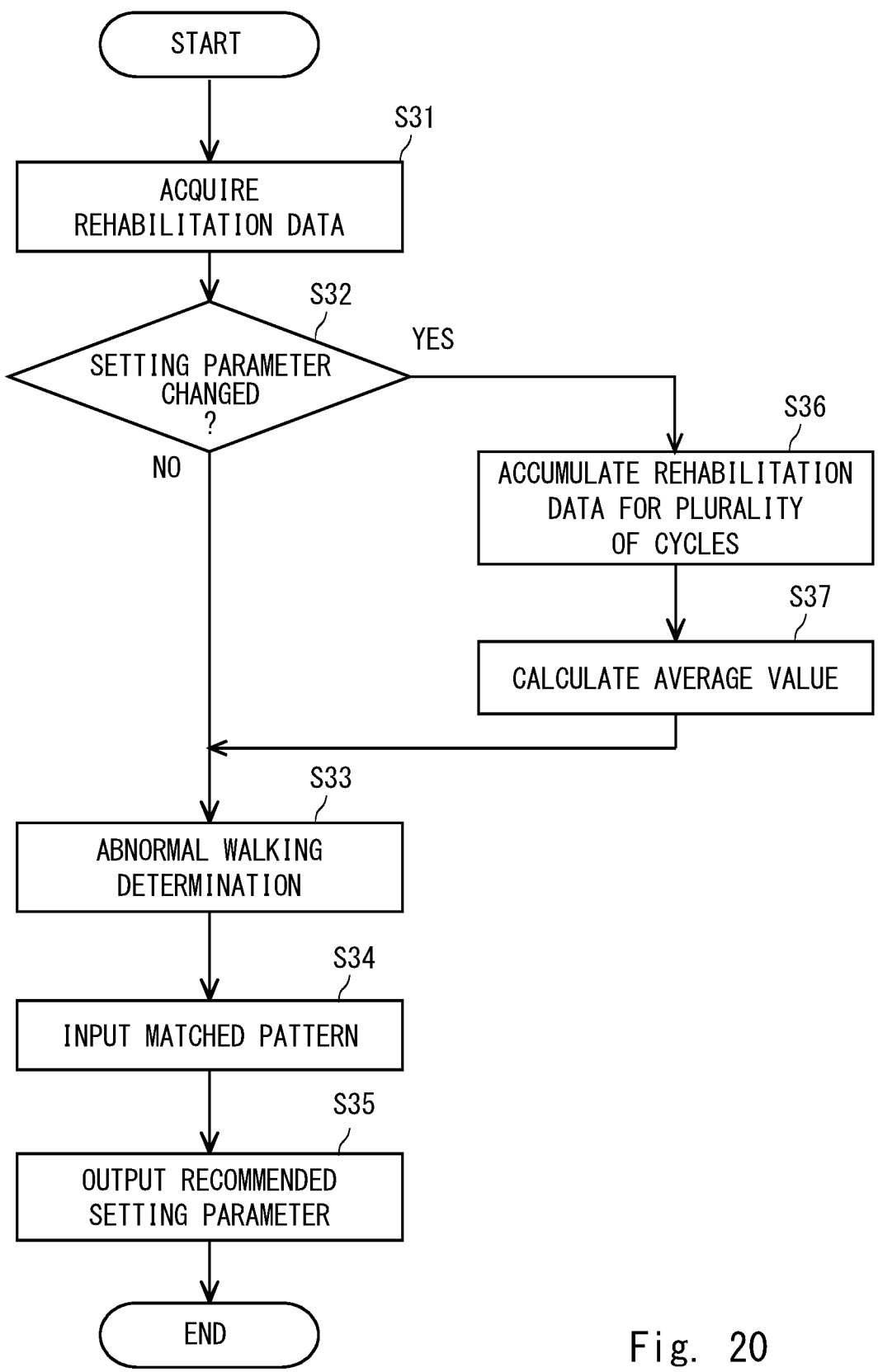
FIG. 20 is a flowchart illustrating processing in a modified example.

With reference to FIG. 20, an operation method according to this embodiment will be described. FIG. 20 is flowchart showing an operation method of the walking training apparatus 100. First, the overall control unit 210 acquires the rehabilitation data (S31). In S31, the overall control unit 210 acquires the rehabilitation data for each walking cycle. Then the overall control unit 210 determines whether the setting parameter has been changed (S32). That is, the overall control unit 210 compares the rehabilitation data between two consecutive walking cycles and determines whether the setting value of the setting parameter has been changed.

When there is no change in the setting parameter (NO in S32), the walking evaluation unit 210a performs abnormal walking determination (S33). The overall control unit 210 inputs the matched pattern that matches the abnormal walking criteria in the trained model (S34). Then the associated setting parameter is output (S35). Since Steps S31, S33, S34, and S35 are similar to Steps S21-S24 in FIG. 16, descriptions thereof will be omitted.

When there is a change in the setting parameter (YES in S32), the walking evaluation unit 210a accumulates the rehabilitation data for a plurality of cycles (S36). Then the walking evaluation unit 210a calculates the average value of the detection data for a plurality of cycles (S37). This average value serves as the determination value for determining whether the walking motion of the trainee 900 is abnormal walking. The walking evaluation unit 210a compares the average value, which is the determination value, with the reference value, and performs abnormal walking determination (S33). The overall control unit 210 inputs the matched pattern that matches the abnormal walking criteria in the trained model (S34). Then the associated setting parameter is output (S35).

With reference to FIG. 21, Steps S36 and S37 will be described in detail. FIG. 21 is a table illustrating the rehabilitation data that has been collected. Each of the data sets corresponds to the data of one walking cycle. That is, FIG. 21 shows the rehabilitation data at the first to fourth cycles as data sets 1 to 4, respectively.

It is assumed here that the setting parameter is changed between the first cycle and the second cycle. In this case, the walking evaluation unit 210a averages the detection data in the second to fourth cycles, thereby obtaining the determination value. For example, it is assumed that the values of the distance $X_1$, which is the determination value of the first abnormal walking pattern, in the second to fourth cycles are $X_{12}$, $X_{13}$, and $X_{14}$, respectively. In this case, in the second cycle, the walking evaluation unit 210a performs abnormal walking determination by calculating $(X_{12}+X_{13}+X_{14})/3$ as the determination value.

According to the above configuration, it is possible to perform abnormal walking determination more appropriately. For example, the driving force of the actuator is greatly changed shortly after the change in the setting value of the setting parameter. The trainee 900 cannot follow the change in the driving force, which makes the walking motion unstable. Shortly after the change in the setting parameter, the abnormal walking determination is made based on the average value of the motion amounts for a plurality of cycles. Accordingly, it is possible to perform abnormal walking determination more appropriately.

While the determination value has been obtained by calculating a simple average in the aforementioned description, the determination value may be obtained by calculating a weighted average. Further, the number of walking cycles to be averaged is not limited to three, and may be two or four or more. It is sufficient that the processing according to the modified example be used for at least one of the abnormal walking determination at the learning stage and the abnormal walking determination at the usage stage.

The program can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

Note that the present disclosure is not limited to the above embodiments and may be changed as appropriate without departing from the spirit of the present disclosure.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training system comprising:
   a plurality of actuators configured to assist a walking motion of a trainee;
   a treadmill on which the trainee walks;
   a plurality of sensors provided to detect a plurality of motion amounts in the walking motion of the trainee assisted by the plurality of actuators;
   a control unit configured to control the plurality of actuators in accordance with a plurality of setting parameters,
   an evaluation unit configured to evaluate that, for each of walking cycles of the walking motion, when at least one of the motion amounts matches one of a plurality of predetermined abnormal walking criteria, the walking motion in the walking cycle is an abnormal walking pattern that meets an abnormal walking criterion, and outputs the abnormal walking pattern; and
   an output unit configured to receive the abnormal walking pattern and outputs a setting parameter associated with the abnormal walking pattern, wherein
   the plurality of actuators includes a front pulling unit configured to apply pulling force to a leg of the trainee from front side and a rear pulling unit configured to apply pulling force to the leg of the trainee from a rear side for assisting a swing motion of the leg;
   the plurality of sensors are provided to detect a plurality of motion amounts in the walking motion of the trainee,
   the plurality of the setting parameters includes a speed of the treadmill, the pulling forces of the front pulling unit, a ratio between the pulling forces of the front and rear pulling units,
   the motion amounts include distances along a walking direction from a hip joint to a foot joint of the trainee at a time of swinging of the leg and at a time of landing of the leg.

2. The walking training system according to claim 1, wherein it is determined whether the walking motion of the trainee matches the abnormal walking criteria using an average value of motion amounts for a plurality of walking cycles shortly after a change in the setting value of the setting parameter.

3. The walking training system according to claim 1, wherein the output unit outputs the setting parameter using a trained model,
   wherein the trained model causes a computer to function so as to output a setting parameter that is associated with a matched abnormal walking pattern based on rehabilitation data for evaluation acquired in a walking training system,
   wherein the trained model is a supervised machine learning model generated in a learning system, and
   wherein the learning system comprises;
   a data acquisition unit configured to acquire rehabilitation data from the walking training system;
   a data generation unit configured to generate learning data based on the rehabilitation data; and
   a learning unit configured to perform machine learning using the learning data, wherein
   the data generation unit generates each of the pieces of rehabilitation data in a walking cycle before and after a change in results of evaluation of the abnormal walking pattern as learning data,
   the learning unit sequentially inputs each of the pieces of rehabilitation data in the walking cycle before and after the change in the results of the evaluation as one data set, thereby performing machine learning, and
   the learning unit constructs a learning model that receives the abnormal walking pattern and outputs the setting parameter.

4. An operation method of a walking training system comprising:
   a plurality of actuators configured to assist a walking motion of a trainee;
   a treadmill on which the trainee walks;
   a plurality of sensors provided to detect a plurality of motion amounts in the walking motion of the trainee assisted by the plurality of actuators;
   a control unit configured to control the plurality of actuators in accordance with a plurality of setting parameters, the operation method comprising the steps of:
   evaluating, for each of walking cycles of the walking motion, when at least one of the motion amounts matches one of a plurality of predetermined abnormal walking criteria, that the walking motion in the walking cycle is an abnormal walking pattern that meets an abnormal walking criterion, and outputs the abnormal walking pattern; and receiving the abnormal walking pattern and outputting a setting parameter associated with the abnormal walking pattern, wherein the plurality of actuators includes a front pulling unit configured to apply pulling force to a leg of the trainee from front side and a rear pulling unit configured to apply pulling force to the leg of the trainee from a rear side for assisting a swing motion of the leg;

the plurality of sensors are provided to detect a plurality of motion amounts in the walking motion of the trainee, the plurality of the setting parameters includes a speed of the treadmill, the pulling forces of the front pulling unit, a ratio between the pulling forces of the front and rear pulling units, the motion amounts include distances along a walking direction from a hip joint to a foot joint of the trainee at a time of swinging of the leg and at a time of landing of the leg.

5. The operation method of the walking training system according to claim 4, wherein it is determined whether the walking motion of the trainee matches the abnormal walking criteria using an average value of motion amounts for a plurality of walking cycles shortly after a change in the setting value of the setting parameter.

6. The operation method of the walking training system according to claim 4, comprising outputting the setting parameter using a trained model, wherein the trained model causes a computer to function so as to output a setting parameter that is associated with a matched abnormal walking pattern based on rehabilitation data for evaluation acquired in a walking training system, wherein the trained model is a supervised machine learning model generated in a learning system, and wherein the learning system comprises;

a data acquisition unit configured to acquire rehabilitation data from the walking training system;

a data generation unit configured to generate learning data based on the rehabilitation data; and a learning unit configured to perform machine learning using the learning data, wherein the data generation unit generates each of the pieces of rehabilitation data in a walking cycle before and after a change in results of evaluation of the abnormal walking pattern as learning data, the learning unit sequentially inputs each of the pieces of rehabilitation data in the walking cycle before and after the change in the results of the evaluation as one data set, thereby performing machine learning, and the learning unit constructs a learning model that receives the abnormal walking pattern and outputs the setting parameter.

* * * * *